(12) United States Patent
Allen et al.

(10) Patent No.: US 10,775,380 B2
(45) Date of Patent: Sep. 15, 2020

(54) RARE CELL ISOLATION DEVICE AND METHOD OF USE THEREOF

(71) Applicant: TumorGen, Inc., San Diego, CA (US)

(72) Inventors: Jeffrey K. Allen, San Diego, CA (US); Alexander G. Allen, Philadelphia, PA (US); Austin E. Allen, San Jose, CA (US)

(73) Assignee: TUMORGEN, INC., San Diego, CA (US)

(*) Notice: Subject to any disclaimer, the term of this patent is extended or adjusted under 35 U.S.C. 154(b) by 157 days.

(21) Appl. No.: 15/565,122

(22) PCT Filed: Apr. 5, 2016

(86) PCT No.: PCT/US2016/026041
§ 371 (c)(1),
(2) Date: Oct. 6, 2017

(87) PCT Pub. No.: WO2016/164359
PCT Pub. Date: Oct. 13, 2016

(65) Prior Publication Data
US 2018/0106805 A1 Apr. 19, 2018

Related U.S. Application Data

(60) Provisional application No. 62/146,047, filed on Apr. 10, 2015.

(51) Int. Cl.
*B01L 3/00* (2006.01)
*G01N 33/574* (2006.01)
(Continued)

(52) U.S. Cl.
CPC .. *G01N 33/57407* (2013.01); *B01L 3/502715* (2013.01); *B01L 3/502738* (2013.01);
(Continued)

(58) Field of Classification Search
None
See application file for complete search history.

(56) References Cited

U.S. PATENT DOCUMENTS 7,888,466 B2   2/2011  Li
9,128,091 B2   9/2015  Toner et al.
(Continued)

FOREIGN PATENT DOCUMENTS

WO   WO-2016164359 A1   10/2016

OTHER PUBLICATIONS

Bacelli et al. Identification of a population of blood circulating tumor cells from breast cancer patients that initiates metastasis in a xenograft assay. Nature Biotech 31(6):539-544 (2013).
(Continued)

*Primary Examiner* — Rebecca M Giere
(74) *Attorney, Agent, or Firm* — Wilson Sonsini Goodrich & Rosati

(57) ABSTRACT

This invention concerns patentable devices configured to capture cancer stem cells and cell clusters. After capturing such cells and/or clusters, the cancerous cells are subjected to whole genome sequencing. The resulting genomic sequence information is then compared to that for "normal" or non-diseased tissue (obtained, for example, from either the same patient, or a population sample, etc.) in order to identify the specific genetic mutation(s) present in the CSCs. Further analysis then correlates the genetic mutations with cell growth signaling pathways typically found with tumor metastases. Armed with this information, an oncologist can then develop a specifically targeted therapy that utilizes approved drugs or drug candidates undergoing clinical testing to address the identified driver mutations and thus effect a "targeted" therapy tailored to the particular patient's disease.

14 Claims, 22 Drawing Sheets

(51) Int. Cl.
- *G01N 33/543* (2006.01)
- *C12M 1/00* (2006.01)
- *C12Q 1/68* (2018.01)
- *C12Q 1/6869* (2018.01)
- *G01N 33/548* (2006.01)
- *G01N 33/58* (2006.01)
- *G01N 27/447* (2006.01)
- *G01N 30/88* (2006.01)

(52) U.S. Cl.
CPC ....... *B01L 3/502761* (2013.01); *C12M 47/04* (2013.01); *C12Q 1/68* (2013.01); *C12Q 1/6869* (2013.01); *G01N 33/548* (2013.01); *G01N 33/54386* (2013.01); *G01N 33/57492* (2013.01); *G01N 33/582* (2013.01); *B01L 2200/0652* (2013.01); *B01L 2200/12* (2013.01); *B01L 2300/0636* (2013.01); *B01L 2300/0816* (2013.01); *B01L 2300/0851* (2013.01); *B01L 2300/0883* (2013.01); *B01L 2300/1822* (2013.01); *B01L 2400/0415* (2013.01); *B01L 2400/0418* (2013.01); *B01L 2400/0677* (2013.01); *B01L 2400/086* (2013.01); *G01N 27/44791* (2013.01); *G01N 2030/8813* (2013.01); *G01N 2800/52* (2013.01)

(56) References Cited

U.S. PATENT DOCUMENTS

| | | |
|---|---|---|
| 9,138,743 B2 | 9/2015 | Yager et al. |
| 2003/0224426 A1 | 12/2003 | Li |
| 2003/0224436 A1 | 12/2003 | Nelson et al. |
| 2011/0294187 A1 | 12/2011 | Toner |
| 2012/0171698 A1 | 7/2012 | Yager et al. |
| 2012/0270209 A1 | 10/2012 | Shah et al. |
| 2014/0154703 A1 | 6/2014 | Skelley et al. |

OTHER PUBLICATIONS

PCT/US2016/026041 International Preliminary Report on Patentability dated Oct. 10, 2017.
PCT/US2016/026041 International Search Report and Written Opinion dated Sep. 15, 2016.
Zardavas et al. Emerging targeted agents in metastatic breast cancer. Nature Reviews Clin Oncol 10:191-210 (2013).
Zong et al. Genome-Wide Detection of Single Nucleotide and Copy Number Variations of a Single Human Cell. Science 338(6114):1622-1626 (2012).

| Agent | Trial | Description | Patients(n) |
|---|---|---|---|
| γ-Secretase Inhibitors | | | |
| MK-0752 (Merck) | Phase I (NCT01295632) | Safety and Efficacy in Combination with Ridaforolimus | Metastatic or Locally Advanced Solid Tumour (124) |
| | Phase I-II (NCT00645333) | Dose Escalation in Combination with Docetaxel | Locally Advanced or MBC (30) |
| RO4929097 (Roche) | Phase I (NCT01071564) | Safety in Combination with Vismodegib | HER2-Nonresectable or MBC (46) |
| | Phase I-II (NCT01149356) | Safety and Efficacy in Combination with Exemestane | Locally Advanced or MBC (104) |
| BMS-906024 (Bristol-Myers Squibb) | Phase I (NCT01292655) | Dose Escalation | Advananced or Metastatic Solid Tumours (95) |
| Delta-Like Ligand 4 Inhibitor | | | |
| MEDI0639 (MedImmune) | Phase I (NCT01577745) | Dose Escalation | Advananced Solid Tumours (57) |
| Smoothened Receptor Inhibitors | | | |
| XL139 (Bristol-Myers Squibb) | Phase I (NCT01413906) | Dose Escalation | Solid Tumours (27) |
| | Phase I (NCT00670189) | Dose Escalation | Advanced or Metastatic Solid Tumours (70) |
| Vismodegib | Phase I (NCT01071564) | Safety in Combination with R04929097 | HER2-Nonresectable or MBC (46) |
| PF-04449913 (Pfizer) | Phase I (NCT01286467) | Dose Escalation | Advanced or Metastatic Solid Tumours (70) |
| LDE225 (Novartis) | Phase I (NCT00880308) | Dose Escalation | Advanced Tumours (100) |
| TAK-441 (Millennium) | Phase I (NCT01204073) | Dose Escalation | Advanced Solid Tumours (46) |
| LEQ506 (Novartis) | Phase I (NCT01106508) | Dose Escalation | Advanced Solid Tumours (71) |
| Frizzled Receptor Inhibitors | | | |
| OMP-18R5 (Oncomed) | Phase I (NCT01345201) | Dose Escalation | Advanced or Metastatic Solid Tumours (44) |
| OMP-54F28 (Oncomed) | Phase I (NCT01608867) | Dose Escalation | Advanced or Metastatic Solid Tumours (36) |
| β-Catenin Inhibitors | | | |
| PRI-724 (Prism Pharma) | Phase I (NCT01302405) | Dose Escalation | Advanced Solid Tumours (64) |
| Porcupine Inhibitors | | | |
| LGK974 (Novartis) | Phase I (NCT01351103) | Dose Escalation | Melanoma (Except Uveal), Lobular or Triple-Negative BC, or Pancreatic Adenocarcinoma (80) |

Abbreviations: BC, Breast Cancer; MBC, Metastatic Breast Cancer.

FIG. 5

| Marker Patterns for CSCs | |
|---|---|
| Acute Myelogenic Leukemia (AML) | $CD34^+/CD38^-$ |
| | $CD90^+$ |
| Acute Lymphoblastic Leukemia | $CD34^+/CD38^-/CD19^+$ |
| Bone Sarcoma | $Stro-1^+/CD105^+/CD44^+$ |
| Brain Tumor | $CD133^+$ |
| Breast Cancer | $ESA^+/CD44^+/CD24^{-/low}/lin^{-a}$ |
| | $CD90^{low}/CD44^+$ |
| | $CD44^+/CD24^{-/low}/ALDH1^{high}$ |
| Colon Cancer | $CD133^+$ |
| | $ESA^{high}/CD44^+/(CD116^+)$ |
| | $CD133^+/CD44^+$ |
| | $CD133^+/CD24^-$ |
| Colon Cancer (Metastatic) | $CD133^+/CD44^{low}/CD24^+$ |
| | $CD133^-/CD44^+/CD24^-$ |
| Endometrial Cancer | $CD133^+$ |
| | $SP^+$ |
| Gall Bladder Cancer | $CD133^+/CD44^+$ |
| Gastric Cancer | $CD44^+$ |
| Liver Cancer | $CD133^+/CD44^+$ |
| | $CD90^+$ |
| | $EpCAM^+$ |
| | $CD133^+$ |
| Metastatic Melanoma | $CD20^+$ |
| Ovarian Cancer | $CD133^+/ALDH^+$ |
| | $CD44^+/CD117^+$ |
| Pancreatic Cancer | $CD44^+/CD24^+ESA^+$ |
| Prostate Cancer | $CD44^+/\alpha_2\beta_1^{h1}/CD133^+$ |
| | $CD44^+/CD24^-$ |
| | $SP^+$ |
| Renal Cell Carcinoma | $CD105^+/(CD133^-/CD24^-)$ |
| Head and Neck Cancer | $CD44^+$ |

FIG. 22

RARE CELL ISOLATION DEVICE AND METHOD OF USE THEREOF

CROSS-REFERENCE TO RELATED APPLICATIONS

This application is a 35 USC § 371 National Stage application of International Application No. PCT/US2016/026041 filed Apr. 5, 2016, now pending; which claims the benefit under 35 USC § 119(e) to U.S. Application Ser. No. 62/146,047 filed Apr. 10, 2015. The disclosure of each of the prior applications is considered part of and is incorporated by reference in the disclosure of this application.

FIELD OF THE INVENTION

The present invention relates generally to microfluidic devices and methods, and more particularly to devices and methods for isolating and analyzing rare cells and rare cell clusters, such as cancer stem cells and cancer stem cell clusters in biological samples, as well as to ways of utilizing data and information generated through the use of such devices and methods.

BACKGROUND INFORMATION

Cancer remains a significant burden on society despite decades of research and prevention programs. In the United States alone there will likely be over 1,658,370 new cases of cancer diagnosed in 2015, with an estimated 589,430 dying from the disease. The National Cancer Institute estimates that today over 13 million people in the U.S. are living with cancer. Metastasis typically describes the disease progression where cancer cells originating from the primary tumor spread via several pathways to other organs in the body, initiating new tumors. Greater than 90% of the deaths related to cancer are due to the metastatic processes within cancer.

The National Comprehensive Cancer Network® (NCCN®), a not-for-profit alliance of 23 of the world's leading cancer centers devoted to patient care, research, and education, is dedicated to improving the quality, effectiveness, and efficiency of cancer care. NCCN® updates and publishes clinical practice guidelines, describing recommended treatment protocols appropriate for use by patients, clinicians, and other health care decision-makers. Even today, current NCCN® guidelines frequently classify cancers based on the anatomical site where the primary tumor has been identified, as has been the case historically. Any changes to the NCCN® guidelines typically require extensive clinical evidence demonstrating significant improvement in patient outcomes. Unfortunately, generating that level of evidence typically requires years and for many cancer patients, time runs out.

Genetic sequencing of the tumor cells has the potential to revolutionize how cancer is treated. Cancer therapy within the past several years has seen advances in the use of Next Generation Sequencing (NGS) to characterize tumors in order to identify specific genetic mutations that help to may identify responders to new or existing targeted therapies. However, cancer research has recently begun to illustrate that not all tumor cells within a primary tumor site are identical. Indeed, it is known that up to 69% of somatic mutations cannot be detected across all regions within a tumor. The implications from such findings immediately pose an important therapy treatment question regarding the use of NGS on patient tumor specimen, namely: which cancer cell(s) should be genetically analyzed to reveal the significant driver mutations resulting in cancer metastasis? Perhaps the best answer would be to identify the set of cancer cells most likely to be involved with tumor metastasis, which ultimately causes the vast majority of patient deaths due to cancer.

An increasing body of evidence has recently appeared in the scientific literature suggesting the existence of cancer stem cells (CSCs). This research indicates that a rare subset of cancer cells may be responsible for the initiation of tumors outside and away from the primary tumor. More recent scientific evidence is beginning to suggest that traditional, non-targeted chemotherapy may actually be increasing the number of CSCs, which may explain a resurgence of the disease in numerous patients following initial chemotherapy success. Clearly, additional approaches are needed to better treat cancer.

SUMMARY OF THE INVENTION

The present invention is based on a rare cell or rare cell cluster capture and isolation device that utilizes a microfluidic approach that provides multiple channels, allowing massively parallel processing and faster cell capture compared to a single channel with flow cytometry.

Accordingly, in one aspect, the present invention provides a microfluidic device for capturing a rare cell or rare cell cluster. The device includes a nonporous substrate having downstream of a sample addition port and arrayed in series the following: a) a single or plurality of capture zones connected by one or more valved microfluidic channels, wherein each capture zone comprises a releasable cell capture reagent that specifically binds a rare cell surface marker, the cell capture reagent being immobilized on the nonporous substrate, wherein the one or more microfluidic channels connecting a first capture zone and a second capture zone of the plurality of capture zones contains a rare cell or cell cluster retention element; and optionally, b) a detector for detecting the rare cell or cell cluster bound by the cell capture reagents. The device may further include a separation channel configured to entrain and space individual cells or cell clusters in a fluid stream, the separation channel being downstream of and fluidly connected to the second capture zone, or a third interposed capture zone by one or more valved microfluidic channels; and optionally a collection well fluidly connected to the separation channel by a valved microfluidic channel for collecting the rare cell or cell cluster.

In embodiments, each capture zone includes a different releasable cell capture reagent that specifically binds a different rare cell surface marker. Additionally, in embodiments, the one or more microfluidic channels connecting the second capture zone and the third capture zone of the plurality of capture zones contains a rare cell or cell cluster retention element. In embodiments, the releasable cell capture reagents each are bound to a dissolvable matrix applied to the nonporous substrate within the capture zones, such as an alginate hydrogel.

In another aspect, the invention provides a method of isolating a rare cell or rare cell cluster. The method includes introducing a fluid sample into a microfluidic device as disclosed herein, and causing the rare cell or rare cell cluster of the fluid sample to traverse the plurality of capture zones to the collection well, thereby isolating the rare cell or rare cell cluster. In embodiments, the cells of the sample may be treated with an agent that degrades cell clusters to provide for cells that are separated into individual single cells. The cells may be treated prior to or after separation via applied electrical current to the separation channel.

In another aspect, the invention provides a composition including a population of rare cells isolated by the microfluidic device as disclosed herein. In one aspect, the composition includes unlysed and/or intact cells. In another aspect, the rare cell population includes greater than about 5, 7.5, 10, 50, 100, or 200 rare cells per 100 microliters of sample.

In another aspect, the invention provides a method of obtaining genetic information from a subject. The method includes: a) obtaining a biological sample from the subject; b) isolating a rare cell or rare cell cluster from the biological sample by introducing the sample into a microfluidic device as described herein and causing the rare cell or rare cell cluster of the sample to traverse the plurality of capture zones to the collection well; c) lysing the isolated cells; and d) obtaining genetic information from the cell lysate, thereby obtaining genetic information from the subject. In embodiments, the genetic information is obtained from a single isolated rare cell from the sample. In additional embodiments, the method may further include comparing the genetic information from one single isolate rare cell to genetic information obtained from another single isolated rare cell from the same subject. Such cells include cancer stem cells.

In another aspect, the invention provides a method of diagnosing cancer in a subject. The method includes: a) introducing a fluid sample obtained from the subject into a microfluidic device as disclosed herein and causing a rare cell or rare cell cluster of the fluid sample to traverse the plurality of capture zones; and b) detecting the rare cell or rare cell cluster via the detector, wherein the presence of the rare cell or rare cell cluster is diagnostic for the presence of cancer, thereby diagnosing cancer in the subject. The method may further include analyzing the isolated cells, wherein analysis comprises one or more of image analysis, cell number analysis, cell morphology analysis, polymerase chain reaction (PCR) analysis, sequence analysis, DNA analysis, RNA analysis, gene expression profiling, proteome analysis, metabolome analysis, immunoassays, and nuclear exclusion analysis. Additional analysis includes whole genome sequencing.

In another aspect, the invention provides a method for determining responsiveness of a subject to a therapeutic regime. The method includes: a) introducing a fluid sample obtained from the subject into a microfluidic device of claim 1 and causing a rare cell or rare cell cluster of the fluid sample to traverse the plurality of capture zones; and b) isolating and analyzing the rare cell or rare cell cluster, wherein analysis comprises comparing a parameter of the rare cell or rare cell cluster to a reference parameter, thereby determining the responsiveness of the subject to a therapeutic regime. The method may further include analyzing the isolated cells, wherein analysis comprises one or more of image analysis, cell number analysis, cell morphology analysis, polymerase chain reaction (PCR) analysis, sequence analysis, DNA analysis, RNA analysis, gene expression profiling, proteome analysis, metabolome analysis, immunoassays, and nuclear exclusion analysis. Additional analysis includes whole genome sequencing.

In another aspect, the invention provides a method of determining a targeted therapy in a subject diagnosed with cancer. The method includes: a) diagnosing the subject with cancer, the diagnosing comprising: i) introducing a fluid sample obtained from the subject into a microfluidic device as disclosed herein and causing a rare cell or rare cell cluster of the fluid sample to traverse the plurality of capture zones; and ii) detecting the rare cell or rare cell cluster via the detector, wherein the presence of the rare cell or rare cell cluster is diagnostic for the presence of cancer; b) performing while genome sequencing of the rare cell or individual cells of the rare cell cluster; c) determining a driver mutation in the cells of (b); and d) determining a target therapeutic regime, thereby determining a targeted therapy in the subject. The method may further include administering one or more chemotherapeutic agents to the subject.

BRIEF DESCRIPTION OF THE FIGURES

The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

FIG. 5 is a Table showing clinical trials of targeted agents against breast cancer stem cells.

FIG. 13 is a photograph from a light microscope showing a main flow channel and the associated herringbone pattern within the chip which was created using an Objet 30 Scholar 3D Printer® from Stratasys. FIG. 13 depicts two separate Capture Zones 1 and 2 along with three main inlet/outlet fluid ports, 1, 2, 3. Fluid flow may be controlled by turning on/off the fluid ports in different combinations. In this manner flow can be controlled through each side independently or in combination or to move a specimen from one capture zone to another.

FIG. 15 shows Capture Zone 1 along with an expanded view of six individual channels and direction of fluid flow. In the image, a herringbone mask is overlaid atop a channel mask to visualize the final mold. PDMS is cast into the mold so all black regions become PDMS and greyscale regions become hollow channels.

FIG. 16 is a computer generated 3D model of an individual microfluidic channel. Note the herringbone pattern is actually an open chamber on the ceiling of the fluid channel. In embodiments, the microfluidic device incorporates the herringbone pattern either on the ceiling and or the floor of each individual fluidic channel.

FIG. 22 is a table showing example CSC markers suitable for detection using the present invention.

DETAILED DESCRIPTION

Figure 1:
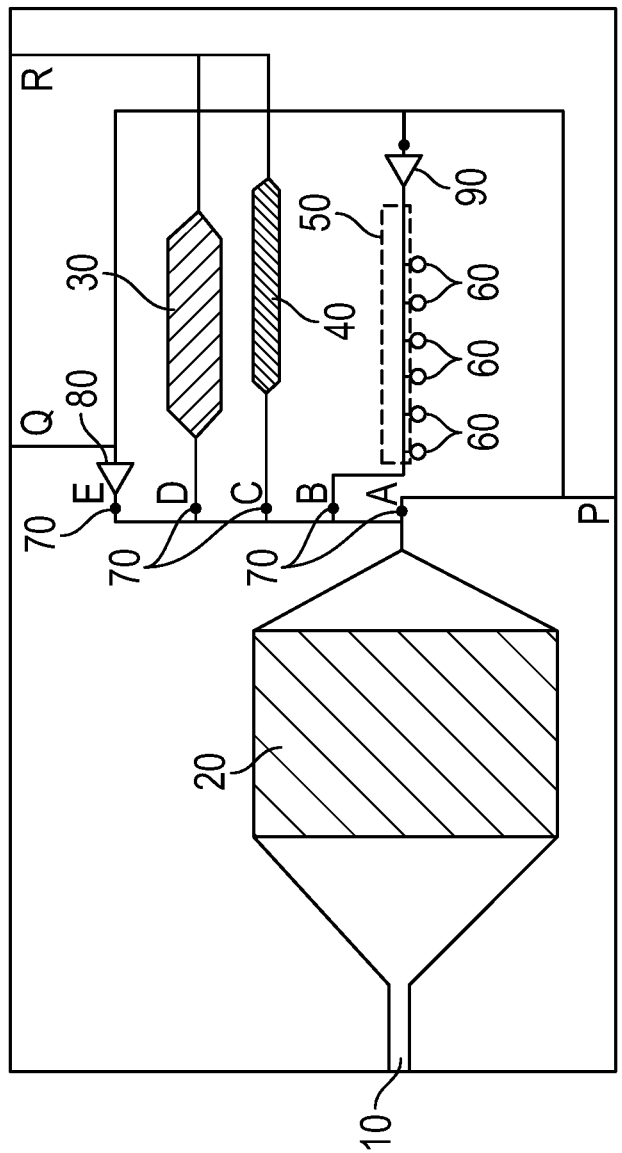
FIG. 1 is a schematic representation of a microfluidic device in one embodiment of the invention.

The present invention relates to devices and methods for diagnosis, differential diagnosis, risk stratification, monitoring, classifying, and determination of treatment regimens in subjects suffering or at risk of suffering from cancer through isolation of rare cells, such as cancer stem cells or stem cell clusters, genetic analysis of such cells to identify driver mutations responsible for the particular cancer, and development of a therapeutic regimen targeted to the genetic basis of patient's particular disease.

Considering the trend of recent data that many solid tumors have cancer stem cells, identifying and capturing these cells in order to elucidate significant driver mutations would allow for major advancements in cancer treatment. Once the genetic mutation(s) in the signaling pathways within the CSCs have been identified, decisions on the availability and/or use of targeted therapies would enable more durable progression free survival (PFS) for the patient.

Currently, flow cytometry is the method typically used to capture CSCs. Flow cytometry methods have several significant limitations that make the routine capture and study of such specialized cells extremely difficult. These limitations include: a single capillary flow path that allows individual cells to pass the detector is simply too slow for large sample volumes (e.g., 10 mls of whole blood); sample preparation may require clusters of cells to be disassociated or broken down into individual cells for optimal flow cytometry performance; and sample preparation steps, prior to analysis, are laborious and technique dependent. Another major limitation of flow cytometry is the method's sensitivity, which at 1 cell in $1\times10^4$ is not sufficient to allow routine capture of rare cells such as CSCs, which may be as rare as one cell among $1\times10^9$ cells.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

A "rare cell" refers to a cell that is typically found in extremely low numbers compared to other cells, for example, 1 cell among $1\times10^9$ red blood cells (RBCs). A "rare cell cluster" refers to groups of rare cells that tend to adhere to each other in small groups commonly referred to as spheroids or mammospheres, which may be composed of different cell types. Rare cells have been identified using varied nomenclature such as: Cancer Stem Cells (CSCs), Circulating Tumor Cells (CTCs), Circulating Tumor Clusters, Circulating Tumor Aggregates, Endothelial Progenitor Cells (EPCs), and Metastasis Initiating Cells (MICs). Herein, unless otherwise indicated, the term "CSC" includes any, some, or all such terms unless the context otherwise requires.

The term "risk" relates to the possibility or probability of a particular event occurring either presently, or, at some point in the future. "Risk stratification" refers to an arraying of known clinical risk factors to allow physicians to classify patients into a low, moderate, high or highest risk of developing of a particular disease, disorder, or condition.

"Diagnosing" includes determining, monitoring, confirmation, subclassification, and prediction of the relevant disease, complication, or risk. "Determining" relates to becoming aware of a disease, complication, risk, etc. "Monitoring" relates to keeping track of an already diagnosed disease, complication, or risk factor, e.g., to analyze the progression of the disease or the influence of a particular treatment on the progression of disease or complication. "Confirmation" relates to the strengthening or substantiating of a diagnosis already performed using other indicators or markers. "Classification" or "subclassification" relates to further defining a diagnosis according to different subclasses of the diagnosed disease, disorder, or condition, e.g., defining according to mild, moderate, or severe forms of the disease or risk. "Prediction" relates to prognosing a disease, disorder, condition, or complication before other symptoms or markers have become evident or have become significantly altered.

A "subject" is a member of any animal species, preferably a mammalian species, optionally a human. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology. The subject can be an apparently healthy individual, an individual suffering from a disease, or an individual being treated for a disease. A "reference subject" or "reference subjects" is/are an individual or a population that serves as a reference against which to assess another individual or population with respect to one or more parameters.

The term "normal" or "clinically normal" means the subject has no known or apparent or presently detectable disease or dysfunction correlated with a disease, particularly a cancer.

An "analyte" refers to the substance to be detected, which may be suspected of being present in the sample (i.e., the biological sample). The analyte can be any substance for which there exists a naturally occurring specific binding partner or for which a specific binding partner can be prepared. Thus, an analyte is a substance that can bind to one or more specific binding partners in an assay.

A "binding partner" is a member of a binding pair, i.e., a pair of molecules wherein one of the molecules binds to the second molecule. Binding partners that bind specifically are termed "specific binding partners." In addition to antigen and antibody binding partners commonly used in immunoassays, other specific binding partners can include biotin and avidin (or streptavidin), carbohydrates and lectins, nucleic acids with complementary nucleotide sequences, effector ligands and receptor molecules, cofactors and enzymes, enzyme inhibitors and enzymes, aptamers and their specific target molecules, and the like. Furthermore, specific binding partners can include partner(s) that is/are analog(s) of the original specific binding partner, for example, an analyte-analog. Immunoreactive specific binding partners include antigens, antigen fragments, antibodies and antibody fragments, both monoclonal and polyclonal, and complexes thereof, including those formed by recombinant DNA methods.

As used herein, the term "epitope" or "epitopes," or "epitopes of interest" refer to a site(s) on any molecule that is recognized and is capable of binding to a complementary site(s) on its specific binding partner. The epitope-bearing molecule and specific binding partner are part of a specific binding pair. For example, an epitope can be a polypeptide, protein, hapten, carbohydrate antigen (such as, but not limited to, glycolipids, glycoproteins or lipopolysaccharides) or polysaccharide and its specific binding partner. Typically an epitope is contained within a larger molecular framework (e.g., in the context of an antigenic region of a protein, the epitope is the region or fragment of the protein having the structure capable of being bound by an antibody reactive against that epitope) and refers to the precise residues known to contact the specific binding partner. As is known, it is possible for an antigen or antigenic fragment to contain more than one epitope.

As used herein, "specific" or "specificity" in the context of an interaction between members of a specific binding pair (e.g., an antigen and antibody, an aptamer and its specific biomolecular target, etc.) refers to the selective reactivity of the interaction. The phrase "specifically binds to" and analogous terms thereof refer to the ability of one member of a binding pair to specifically bind to (e.g., preferentially react with) to the other member of the binding pair and not to bind specifically to other entities. Antibodies, antibody fragments, and other binding pair members that specifically bind to another molecule correlated with cancer can be identified, for example, by diagnostic immunoassays (e.g., radioimmunoassays ("RIA") and enzyme-linked immunosorbent assays ("ELISAs"), surface plasmon resonance, or other techniques known to those of skill in the art. In one embodiment, the term "specifically binds" or "specifically reactive" indicates that the binding preference (e.g., affinity) for the target analyte is at least about 2-fold, more preferably at least about 5-fold, 10-fold, 100-fold, 1,000-fold, a million-fold or more over a non-specific target molecule (e.g., a randomly generated molecule lacking the specifically recognized site(s)).

An antigen, antibody, or other analyte "correlated" or "associated" with a disease, particularly cancer refers to an antigen antibody, or other analyte as the case may be that is positively correlated with the presence or occurrence of cancer generally or a specific type of cancer, as the context requires. In general, an "antigen" is any substance that exhibits specific immunological reactivity with a target antibody. Suitable antigens may include, without limitation, molecules comprising at least one antigenic epitope capable of interacting specifically with the variable region or complementarity determining regions (CDRs) of an antibody or CDR-containing antibody fragment. Antigens typically are naturally occurring or synthetic biological macromolecules such as a protein, peptide, polysaccharide, lipids, or nucleic acids, or complexes containing these or other molecules.

As used herein with reference endogenous cancer (or other disease-associated) antigens (or other analytes correlated with cancer or other disease), the term "elevated level" refers to a level in a sample that is higher than a normal level or range, or is higher that another reference level or range (e.g., earlier or baseline sample). The term "altered level" refers to a level in a sample that is altered (increased or decreased) over a normal level or range, or over another reference level or range (e.g., earlier or baseline sample). The normal level or range for endogenous cancer antigens is defined in accordance with standard practice. Because the levels of a target analyte in some instances will be very low, a so-called altered level or alteration can be considered to have occurred when there is any net change as compared to the normal level or range, or reference level or range that cannot be explained by experimental error or sample variation. Thus, the level measured in a particular sample will be compared with the level or range of levels determined in similar samples of normal tissue. In this context, "normal tissue" is tissue from an individual with no detectable cancer pathology, and a "normal" (sometimes termed "control") patient (i.e., subject) or population is one that exhibits no detectable pathology. The level of an analyte is said to be "elevated" where the analyte is normally undetectable (e.g., the normal level is zero, or within a range of from about 25 to about 75 percentiles of normal populations), but is detected in a test sample, as well as where the analyte is present in the test sample at a higher than normal level.

A "microarray" or "array" refers a device consisting of a substrate, typically a solid support having a surface adapted to receive and immobilize a plurality of different protein, peptide, and/or nucleic acid species (i.e., capture or detection reagents) that can used to, for example, bind to or determine the presence and/or amount of other molecules (i.e., analytes) in biological samples such as blood. "Microarray" or "array" refers to a solid phase support having a planar surface, which carries an array of nucleic acids, each member of the array comprising identical copies of an oligonucleotide or polynucleotide immobilized to a spatially defined region or site, which does not overlap with those of other members of the array; that is, the regions or sites are spatially discrete. Spatially defined hybridization sites may additionally be "addressable" in that its location and the identity of its immobilized oligonucleotide are known or predetermined, for example, prior to its use. Ordered arrays include, but are not limited to, those prepared by photolithography, spotting, printing, electrode arrays, "gel pad" arrays, and the like. The size of array can vary from one element to thousands, tens of thousands, or even millions of elements. Depending on the number of array elements required, some array types or methods of preparing the array may be more advantageous, as those skilled in the art are aware. Typically, the oligonucleotides or polynucleotides are single stranded and are covalently attached to the solid phase support, usually by a 5'-end or a 3'-end. The density of non-overlapping regions containing nucleic acids in a microarray is typically greater than 100 per $cm_2$, and more preferably, greater than 1000 per $cm_2$. As used herein "microarray" or "array" may also refer to a "random microarray" or "random array", which refer to an array whose spatially discrete regions of oligonucleotides or polynucleotides are not spatially addressed. That is, the identity of the attached oligonucleoties or polynucleotides is not discernable, at least initially, from its location. In one aspect, random microarrays are planar arrays of microbeads wherein each microbead has attached a single kind of hybridization tag complement, such as from a minimally cross-hybridizing set of oligonucleotides. Arrays of microbeads may be formed in a variety of ways. Likewise, after formation, microbeads, or oligonucleotides thereof, in a random array may be identified in a variety of ways, including by optical labels, such as fluorescent dye ratios or quantum dots, shape, sequence analysis, or the like.

The term "solid phase" refers to any material or substrate that is insoluble, or can be made insoluble by a subsequent reaction. A solid phase can be chosen for its intrinsic ability to attract and immobilize a capture or detection reagent. Alternatively, a solid phase can have affixed thereto a linking agent that has the ability to attract and immobilize a capture agent. The linking agent can, for example, include a charged substance that is oppositely charged with respect to the capture agent itself or to a charged substance conjugated to the capture agent. In general, a linking agent can be any binding partner (preferably specific) that is immobilized on (said to be "attached to") a solid phase and that has the ability to immobilize a desired capture or detection reagent through a binding or other associative reaction. A linking agent enables the indirect binding of a capture reagent to a solid phase material before the performance of an assay or during the performance of an assay. The solid phase can, for example, be plastic, derivatized plastic, magnetic or non-magnetic metal, glass or silicon, including, for example, a test tube, microtiter well, sheet, bead, microparticle, chip, and other configurations known to those of ordinary skill in the art.

The term "nonporous substrate" means a solid support material or matrix on top of which the microfluidic system of the invention is created using a photolithography or other suitable process. The material is typically poly dimethyl siloxane (PDMS) or poly methyl methacrylate (PMMA) or other suitable materials known in the art.

A "capture zone" refers to a specific area on the microfluidics system that is composed of many separate flow channels based on a herringbone pattern where the channels are coated with a hydrogel matrix. The channels are coated with a hydrogel matrix that have biomolecular binding agents covalently attached with the ability to capture or bind to targeted antigens on the surface of rare cells.

A "cell/cluster retention element" refers to a subsystem within a microfluidics flow path that allows cells or cell clusters to be physically retained while allowing smaller biomolecules and buffers to pass through.

A "separation channel" means a separate subsystem within a microfluidics flow path that allows captured cells, once released, to be separated based on a cells unique size, charge, and surface properties, all of which can be manipulated by buffers and/or coatings on the surface of the separation channel.

A "rare cell/cluster detector" refers to a subsystem within a microfluidics separation channel that can "sense" or detect the passage of either single cells or cell clusters as they pass a fixed point within the channel. Detection can be based on either conductivity with no required label or fluorescence emission from, for example, a pre-labeled antibody or aptamer.

As used herein, term "microparticle" refers to a small particle that is recoverable by any suitable process, e.g., magnetic separation or association, ultracentrifugation, etc. Microparticles typically have an average diameter on the order of about 1 micron or less.

A "capture" or "detection" agent or reagent refers to a binding partner that binds to an analyte, preferably specifically. Capture or detection reagents can be attached to or otherwise associated with a solid phase.

The term "labeled detection reagent" refers to a binding partner that binds to an analyte, preferably specifically, and is labeled with a detectable label or becomes labeled with a detectable label during use in an assay. A "detectable label" includes a moiety that is detectable or that can be rendered detectable. With reference to a labeled detection agent, a "direct label" is a detectable label that is attached, by any means, to the detection agent, and an "indirect label" is a detectable label that specifically binds the detection agent. Thus, an indirect label includes a moiety that is the specific binding partner of a moiety of the detection agent. Biotin and avidin are examples of such moieties that can be employed, for example, by contacting a biotinylated antibody with labeled avidin to produce an indirectly labeled antibody.

The term "indicator reagent" refers to any agent that is contacted with a label to produce a detectable signal. Thus, for example, in conventional enzyme labeling, an antibody labeled with an enzyme can be contacted with a substrate (the indicator reagent) to produce a detectable signal, such as a colored reaction product.

An "antibody" refers to a protein consisting of one or more polypeptides substantially encoded by immunoglobulin genes or fragments of immunoglobulin genes. This term encompasses polyclonal antibodies, monoclonal antibodies, and antigen-binding fragments thereof, as well as molecules engineered from immunoglobulin gene sequences. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Antibodies are generally found in bodily fluids, mainly blood.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains, respectively.

Antibodies exist as intact immunoglobulins or as a number of well-characterized fragments produced by digestion with various peptidases. Thus, for example, pepsin digests an antibody below the disulfide linkages in the hinge region to produce F(ab')2, a dimer of Fab which itself is a light chain joined to VH-CH1 by a disulfide bond. The F(ab')2 may be reduced under mild conditions to break the disulfide linkage in the hinge region thereby converting the (Fab)2 dimer into a Fab' monomer. The Fab' monomer is essentially a Fab with part of the hinge region. While various antibody fragments are defined in terms of the digestion of an intact antibody, one of skill will appreciate that such Fab' fragments may be synthesized de novo either chemically or by utilizing recombinant DNA methodology. Thus, in the context of the invention, the term "antibody" also includes antigen-binding antibody fragments either produced by the modification of whole antibodies or synthesized de novo using recombinant DNA methodologies. Antibodies include single chain antibodies (antibodies that exist as a single polypeptide chain), single chain Fv antibodies (sFv or scFv), in which a variable heavy and a variable light chain are joined together (directly or through a peptide linker) to form a continuous polypeptide. The single chain Fv antibody is a covalently linked VH-VL heterodimer that may be expressed from a nucleic acid including VH- and VL-encoding sequences either joined directly or joined by a peptide-encoding linker. While the VH and VL are connected to each as a single polypeptide chain, the VH and VL domains associate non-covalently. The scFv antibodies and a number of other structures convert the naturally aggregated, but chemically separated, light and heavy polypeptide chains from an antibody V region into a molecule that folds into a three dimensional structure substantially similar to the structure of an antigen-binding site are known to those of skill in the art.

An "aptamer" refers to a synthetic oligonucleotide or peptide molecule that binds to a specific target biomolecule, for example, a specific cell surface protein. In addition to their discriminate recognition, aptamers offer advantages over antibodies as they can be engineered completely in a test tube, can be readily produced by chemical synthesis, and possess desirable storage properties. Nucleic acid aptamers are oligonucleotide species that have been engineered through repeated rounds of in vitro selection or, equivalently, SELEX. Both DNA and RNA aptamers show robust binding affinities for various targets. Peptide aptamers are proteins that are designed to bind to specific proteins. They typically consist of a variable peptide loop of about 10-20 amino acids attached at both ends to a protamersein scaffold. This double structural constraint greatly increases the binding affinity of peptide aptamers to levels comparable to an antibody's (nanomolar range). Peptide aptamers can be selected using different systems, including a yeast two-hybrid system as well as from biopanning combinatorial peptide libraries constructed by, for example, phage display.

A "panel" refers to a group of two or more distinct molecular species that have shown to be indicative of or otherwise correlated with a particular disease or health condition. Such "molecular species" may be referred to as "biomarkers", with the term "biomarker" being understood to mean a biological molecule the presence or absence of which serves as an indicator of a particular biological state, for example, the occurrence (or likelihood of the occurrence) of cancer in a subject. In other words, a biomarker is a characteristic that can be objectively measured and evaluated as an indicator of normal biologic processes, pathogenic processes, or pharmacologic responses to a therapeutic intervention. In the context of the invention an "assay panel" or "array panel" refers to an article, typically a solid phase substrate, having a panel of capture reagents associated therewith (typically by immobilization), wherein at least one of the capture reagents is specifically reactive with an endogenous cancer antigen present on the surface of a CSC. In some embodiments, an assay panel includes 1, 2, 3, 4, 5, 6, 7, 8, 9, 10, 11, 12, 13, 14, 15, 16, 17, 18, 19, 20, or more (e.g., 25, 30, 35, 40, 50, 75, 100, 150, 200, 250, 500, etc., including any integer, or range of integers from 1 to 500) different detection reagents that are proteinaceous cancer-associated antigens, alone or combination with other detection reagents (e.g., nucleic acid-based detection reagents, etc.) correlated with the presence of disease (e.g., cancer) in a subject.

A "biological sample" is a sample of biological material taken from a patient or subject. Biological samples include samples taken from bodily fluids and tissues (e.g., from a biopsy) or tissue preparations (e.g., tissue sections, homogenates, etc.). A "bodily fluid" is any fluid obtained or derived from a subject suitable for use in accordance with the invention. Such fluids include whole blood, blood fractions such as serum and plasma, urine, sweat, lymph, feces, ascites, seminal fluid, sputum, nipple aspirate, post-operative seroma, wound drainage fluid, saliva, synovial fluid, ascites fluid, bone marrow aspirate, cerebrospinal fluid, nasal secretions, amniotic fluid, bronchoalveolar lavage fluid, pleural effusion, peripheral blood mononuclear cells, total white blood cells, lymph node cells, spleen cells, and tonsil cells.

A "companion diagnostic" is a diagnostic test designed to identify subgroups of patients who may or may not benefit from a particular drug, who may have adverse reactions to the drug, or may require different dosages of the drug.

The term "drug rescue" refers to a drug or drug candidate in the context of the reevaluation of samples and/or data from discontinued clinical trials or pre-clinical development with new or improved evaluation methods.

An "alginate hydrogel" refers to an anionic polysaccharide-based biopolymer. Crosslinking of the gel can be achieved via calcium ions. Alginate hydrogels can be utilized as support structures for tissue engineering, as delivery vehicles for pharmaceuticals, and as model systems for extracellular matrices used in basic biological studies. The addition of chelating reagents which will tie up the calcium ion cross linker will rapidly dissolve an alginate hydrogel.

A "Peltier valve" means a valve that can be actuated by the freezing or heating (thawing) of a buffer reagent within a designated area on a microfluidics channel. The cooling and heating element is a Peltier device, which is also called a Peltier cooler, heater, or thermoelectric heat pump that is essentially a solid-state active heat pump that transfers heat from one side of the device to the other, using electrical energy. Some main advantages of a Peltier cooler are that it contains no moving parts or circulating compression liquids and is small in size and flexible in shape. A frozen Peltier valve can essentially block the flow of reagents in a microfluidic channel, while reversing the electric current will heat the Peltier device to thaw the frozen buffer, thereby opening the valve.

A "plurality" means more than one.

The term "sample profiling" refers to a representation of information relating to the characteristics of a biological sample, for example, serum, recorded in a quantified way in order to determine patterns or signatures of biomolecules in the particular sample.

As used herein, the term "about" refers to approximately a +/−10% variation from the stated value. It is to be understood that such a variation is always included in any given value provided herein, whether or not it is specifically referred to.

The present invention is based on a rare cell or cell cluster capture and isolation device that utilizes a microfluidic approach that provides hundreds of channels, allowing massively parallel processing and faster cell capture compared to a single channel with flow cytometry.

With reference to FIG. 1, the present invention provides a microfluidic device for capturing a rare cell or rare cell cluster from a fluid sample. The device of the invention, utilizes one, two, three, four or more separate cell capture zones in addition to a cell/cluster separation zone or channel (e.g., an electro-osmotic separation zone), to ultimately isolate both individual rare cells in addition to rare cell clusters or small grouped cell aggregates. The clusters or cell aggregates are an important morphological characteristic that differentiates cells likely to form new metastatic tumors from other non-progenitor tumor cells. Several of the design features of the instant device are intended to preserve nucleated cell aggregates that exhibit intercellular adhesion to support the clusters. As will be appreciated, all isolated cells or cell clusters preferably express the surface antigens bound by the corresponding antibodies (or other capture reagents) used in the device's multiple capture zones. All other cells, such as non-nucleated RBCs or cells with only one of the capture antigens, are eluted as waste from the device during the process of performing an assay on the device.

Accordingly, the device includes a nonporous substrate having a series of components wherein fluid flow is controlled in a downstream manner to effectuate isolation of rare cells or rare cell clusters. In the embodiment shown in FIG. 1, the device includes a sample addition port (10), a plurality of capture zones (20, 30 and 40), a separation channel (50) and one or more collection wells (60), all fluidly connected via valved (70) microfluidic channels. As discussed further below, each capture zone (20, 30 and 40) includes one or more releasable cell capture reagents. While FIG. 1 depicts a device having a first (20), second (30) and third (40) capture zone, one of skill in the art would appreciate that any number of capture zones may be utilized.

The cell capture reagents specifically bind a rare cell surface marker, wherein different cell capture reagents which specifically bind different rare cell surface markers may be immobilized in each capture zone. However, in embodiments, cell capture reagents may be used which specifically bind non-rare cells, such as leukocytes, so that those cells may be targeted to achieve further separation of these contaminating cells, e.g., non-rare cells.

Cell capture reagents are immobilized on the nonporous substrate within capture zones by, for example a dissolvable matrix which is dissolved in a controlled fashion to allow cells that have become immobilized in a particular capture zone via binding to the cell capture reagent to become soluble thus allowing their flow to a downstream component of the device, such as a downstream capture zone. In one embodiment, the dissolvable matrix is a hydrogel, such as an alginate hydrogel which may be dissolved by a dissolution buffer or agent. Dissolution buffers include those having a chelating agent which acts to dissolve crosslinking of the hydrogel, such as EDTA, EGTA or sodium citrate. Dissolution agents may also be used, such as enzymes.

In embodiments, microfluidic channels are coated with an alginate hydrogel which has been derivatized with a covalently bonded streptavidin bio-affinity molecule. Any antibody with a biotin molecule attached can be attached to a alginate-streptavidin modified hydrogel. The attached antibody once immobilized on the alginate hydrogel can bind to the surface antigen of a rare cell or rare cell cluster thus retaining the live cell while other cells are washed away. Individual capture zones can be uniquely modified for a specific antibody therefore multiple capture zones used in series or parallel can be used to capture multiple surface antigens and therefore multiple cell types.

The device is ideally described with reference to fluid flow through the device. The following is an example of a flow sequence for the isolation rare cell cells from a sample, such as whole blood. Prior to the addition of any biological specimen, all microfluidic channels of the device are flushed with an isotonic buffer, such as phosphate buffered saline (PBS). The embodiment shown in FIG. 1 will be discussed as having Peltier valves. However, it will be appreciated that any number of valves as generally known in the art of microfluidics may be utilized, such as pressure valves, electrostatic valves, mechanical valves and the like. Proper function of Peltier frozen valves requires buffer and/or other reagents to be within close proximity of the microfluidic channel immediately above or below the Peltier valve.

Flow through the device may begin with freezing, i.e., closing of Peltier valves B, C, D and E, while keeping Peltier valve A thawed (i.e., open). The device is then ready for perfusion with a fluid sample. In one embodiment a 10 ml whole blood specimen is taken from a heparinized vacutainer tube that is directly connected to the device via 18 gauge blood infusion tubing attached to the sample addition port (10). Directly infusing the whole blood sample from the primary blood collection tube minimizes the risk of rare cells non-specifically binding to the walls of any other vessel, separate centrifuge tube, or pump cylinder.

A vacuum source is applied to the device downstream of the first capture zone (20) at, for example channel P thereby drawing the sample through channels of the first capture zone (20) and then to waste though channel P since Peltier valves B, C, D and E are closed. Target rare cells/clusters with a first specific rare cell surface antigen are retained in the first capture zone (20), which may include a cell capture reagent, such as a detectably labeled antibody which specifically binds the specific rare cell surface antigen. In one embodiment, the cell capture agent is a fluorescently labeled antibody specific for the specific rare cell antigen, the antibody being covalently cross-linked to the dissolvable hydrogel, such as alginate hydrogel which is present within the first capture zone (20). The vast majority of cells in a blood sample are red blood cells (RBCs), which are flushed through the first capture zone (20) and into waste with minimal lysis of cells since the channel dimensions are sufficiently wide to keep any flow shear forces to a low level.

To ensure flow shear forces are maintained at a low level, microfluidic channels of the device through with rare cells are intended to flow, such as those fluidly connecting capture zone, are between about 60 and 450 μm in diameter.

Following introduction of the sample to the first capture zone (20), a wash buffer (e.g., isotonic buffer with calcium chloride) is pulled through the system, again via vacuum at channel P to flush cellular debris or non-bound cells within the first capture zone (20) into waste. At this point only cells expressing the first specific rare cell surface antigen are retained in the first capture zone (20).

The next flow sequence begins with freezing of Peltier valves A, B, C, and D and thawing or opening Peltier valve E. A dissolution buffer, such as EDTA is then directed to flow through the first capture zone (20), which dissolves the hydrogel, thus releasing the cells along with the cells having bound cell capture reagent attached. The cells with bound cell capture reagent are directed through the microfluidic channel directly in line with a rare cell or cell cluster retention element (80). In embodiment, the rare cell or cell cluster retention element is referred to as a "C-Comb filter", and may be a microfluidic filter that includes fingers or mesh spaced so as to retain cells on the upstream side of the filter. In one embodiment, the retention element has multiple channels with dimensions of approximately 5 μm×5 μm; therefore, rare cells and clusters are retained on the upstream side of the filter while unbound antibodies, buffer, cellular debris, and the like, will easily pass through. An isotonic wash buffer is then flushed through the system, including through retention element (80) to remove residual dissolution buffer and ensure that integrity of cells and cellular aggregates.

The next flow sequence begins with freezing of Peltier valves A, B, and C and thawing or opening Peltier valves D and E. Wash buffer is allowed to flow from a second input (Q), which will flush cells retained by the retention element (80) into a second capture zone (30), which contains a cell capture reagent, such as fluorescently labeled antibodies specific for a second rare cell specific surface antigen that have been covalently bound to hydrogel present in the second capture zone (30). Cells and cell clusters that lack the second rare cell specific surface antigen are not retained and allowed to flow to waste. At this point in the flow sequence, only cells with both the first and second specific rare cells surface antigens are retained in the second capture zone (30). Next, dissolution buffer (e.g., EDTA) is pumped through via a third input (R) to dissolve the hydrogel of the second capture zone (30) thereby allowing cells positive for both the first and second rare cell antigens to be retained by the retention element (80). Wash buffer (e.g., isotonic buffer with calcium chloride) is again flushed through the device via a third input (R) to wash away any residual dissolution buffer.

The next flow sequence begins by closing Peltier valves A, B, and D and opening Peltier valves C and E. The cells positive for the first and second rare cell specific antigens are retained by the cell retention element (80) are then washed with buffer from the second input (Q) into a third capture zone (40), which contains a third cell capture reagent covalently attached to the hydrogel present in the third capture zone (40). Following cell attachment, wash buffer is then pumped through the third capture zone (40) to wash away cells negative for the third rare cell specific antigen. Dissolution buffer (e.g., EDTA) is then pumped through the third capture zone (40) via the third input (R) to dissolve hydrogel and allow cells positive for each of the first, second and third rare cell specific antigens to be retained by the retention element (80). An optional step at this point may be used to wash away residual dissolution buffer using a calcium chloride wash buffer.

The next flow sequence begins with closing valves A, C and D and opening valves B and E. Cells positive for each of the first, second and third rare cell specific antigens retained by the retention element (80) are then washed with buffer through the separation channel (50) and retained by a second rare cell or cell cluster retention element (90). Once all the retained cells are in the second retention element, the cells are sorted along the separation channel. This may be accomplished by applying a voltage which causes the cells to migrate independently depending on the size and overall charge on the cell-antibody complexes. If desired, cells can be detected by a detector as they pass along the separation channel (50). Detection may be by any number of means, for example, by conductivity or fluorescence emission from labeled antibodies.

Separated cells may then be isolated by collection into one or more individual collection wells (60). For example, as detected cells of interest pass a collection well, the voltage can be switched, for example, to "+" polarity pole for that collection well, thus changing the electroosmotic flow direction into the collection well.

The device may also include an internal control to ensure accuracy of device performance as well as allow statistical analysis of results. The internal control may be introduced along with or separate from the sample and be configured to monitor accurate flow thought the device. For example, in one embodiment, the internal control may be an antigen for which a binding conjugate may be applied to the capture zones such that the control migrates along with rare cells that are present in the sample.

The individual microfluidic channel dimensions have been optimized to capture rare cell clusters and bulk tumor cell clusters. The average cancer stem cell cluster can range between 3 and 30 cells per cluster. A typical white blood cell diameter is 10-12 um, however a cancer stem cell or rare cell cluster is estimated at 35 um to 60 um in diameter. Current microfluidic capture devices are focused on single cell capture with dimensions that would prevent the capture of rare cell clusters. The microfluidic channels of the present invention are coated with an alginate hydrogel which has been derivatized with a covalently bonded streptavidin bioaffinity molecule. Any antibody with a biotin molecule attached can be easily attached to the alginate-streptavidin modified hydrogel. Since the hydrogel coating within the microfluidic channels is approximately 5 um thick, improved binding of rare cells to the immobilized antibody can be achieved by optimizing the number of wall (i.e., hydrogel coating) interactions of the rare cell cluster. Computer modeling of several parameters were performed which provided a set of dimensions which illustrated that the dimensions described will produce the highest number of particle (i.e., rare cell cluster) wall (i.e., hydrogel coating) interactions.

Figure 13:
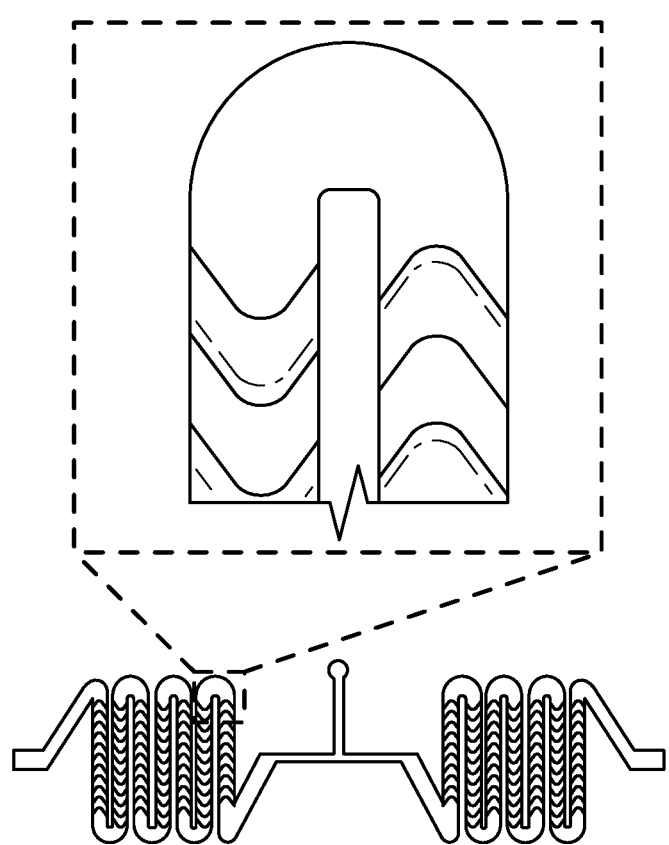
FIG. 13 is an illustration of a microfluidic capture device generated by 3D printing in one embodiment of the invention.
Figure 18:
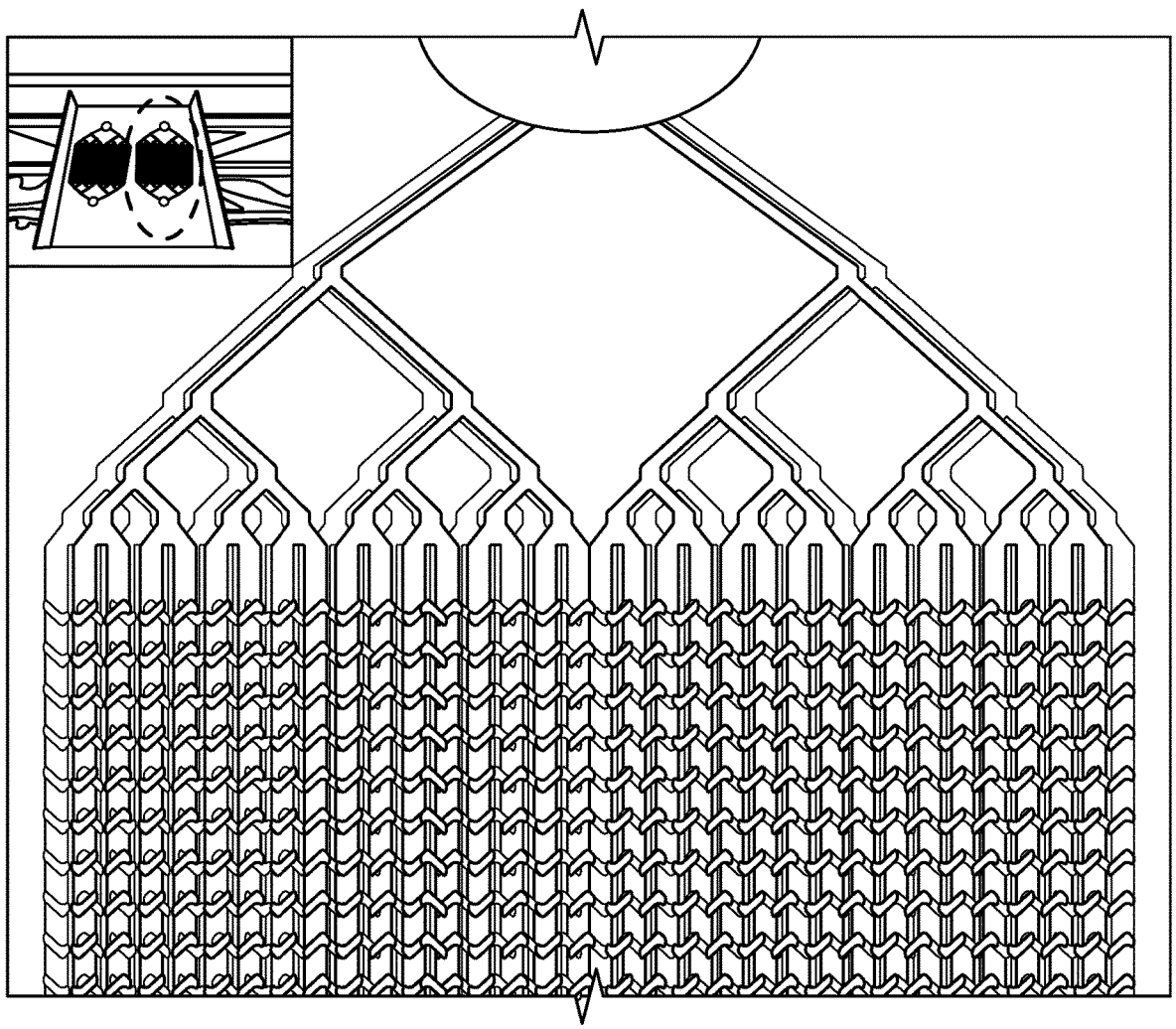
FIG. 18 is an image of a microfluidic device in one embodiment of the invention generated via photolithography from PDMS. Shown is a High-Low Herringbone Configuration (HLHC) of the channels produced via photolithography. The configuration includes 2 separate pieces oxygen plasma bonded together to produce a pattern which includes up to 64 channels (32 from each piece) aligned or offset in parallel and having a total volume of 24.24 µL. In addition, all surfaces are polydimethylsiloxane (PDMS), which eliminates the need for a bottom substrate.
Figure 19:
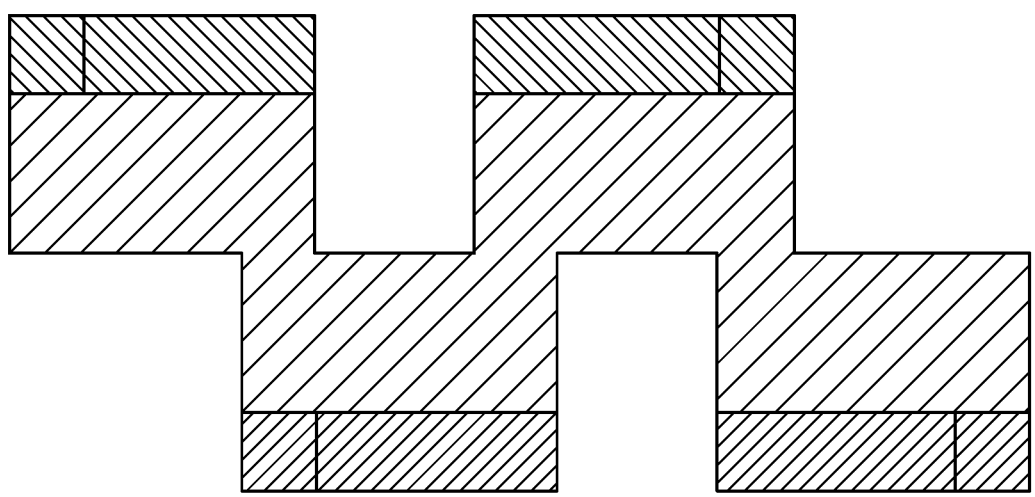
FIG. 19 is a schematic of a cross-section view of channels of the device in FIG. 18. The cross-sectional view shows the ceiling (high) and floor (low) herringbone extension heights which are the shaded top and bottom regions. The figure shows the offset configuration between high and low pattern.

In various embodiments, the channels of the device which include capture zones are arranged in a herringbone configuration. When referring to a "herringbone matrix," the term is meant to refer to the general geometry of a microfluidic chip containing the matrix architecture described herein. A representative herringbone matrix or pattern is shown in FIGS. 13 and 18. In one embodiment, the herringbone matrix is a high-low herringbone configuration as shown in FIGS. 18 and 19. The HLHC comprises channels that are offset from one another and which fluidly connect with one another in an alternating pattern to produce an increased channel surface area for binding. In embodiments, the cross-section of each channel is square or rectangular and each channel is fluidly connected to an adjacent channel. In embodiments, the channels are not offset from one another. Further, a herringbone matrix configuration includes a zigzag shape, for example a zigzag shape having equal angles or a zigzag shape having unequal angles, in particular in the shape of a symmetrical or asymmetrical herringbone pattern, or in the shape of a parallel slash mark [/] pattern, in particular an equidistant parallel slash mark pattern.

In various embodiments, the width of the flow channels can be from about 5 um to about 1000 um and, for larger width flow channels, can be about 100 um, at or between about 100 um and about 150 um, at or between about 150 um and 200 um, at or between about 200 um and 250 um, at or between about 250 um and about 300 um, at or between about 300 um and about 350 um, at or between about 350 um and about 400 um, at or between about 400 um and about 450 um, at or between about 450 um and about 500 um, at or between about 500 um and about 550 um, at or between about 550 um and 600 um, at or between about 600 um and about 650 um, at or between about 650 um and about 700 um, at or between about 700 um and about 750 um, at or between about 750 um and 800 um, at or between about 800 um and about 850 um, at or between about 850 um and about 900 um, at or between about 900 um and about 950 um, at or between 950 um and 1000 um. In many applications, a range of flow channel widths from about 75 um to about 125 um will be preferred. However, in certain instances, channel widths could exceed 1000 um. For narrower channels, the widths can be about 5 um or greater and about 100 um or smaller. Channel widths can be from about 10 um to about 75 um, from about 15 um to about 50 um, and from about 20 um to about 40 um. In some embodiments the channel width is about 5, 10, 15, 20, 25, 30, 35, 40, 45, 50, 55, 60, 65, 70, or 75 um. The height can be from about 5 um to about 100 um, from about 10 um to about 75 um, from about 15 um to about 50 um, and from about 20 to about 40 um. In some embodiments the channel height is about 5, 10, 15, 20, 25, 30, 35, 40, 45, 50, 55, 60, 65, 70, or 75 um. The cross sectional area can be from about 20 to about 13000 $um^2$, from about 50 to about 10000 $um^2$, from about 200 to about 8000 $um^2$, from about 250 to about 5000 $um^2$, from about 500 to about 3000 $um^2$, and in many embodiments, it is preferred to be from about 1400 to about 1600 $um^2$. In some embodiments the cross sectional area is about 500, 600, 700, 800, 900, 1000, 1100, 1200, 1300, 1400, 1500, 1600, 1700, 1800, 1900, or about 2000 $um^2$. The shape of the cross section of the individual channels of the matrix devices of this invention can be the same or different and can take different shapes such as square, rectangular, other polygonal, circular, elliptical, semicircular, semielliptical, and the like. The cross sectional shapes and areas can vary within the same channel and can be prepared by fabrication techniques described earlier and known in the art. Square or rectangular channel geometries are generally favored.

A microfluidic device according to the present may further comprise a microprocessor such as a computer for control of the device. A programmable controller may also be part for controlling the operation of the microfluidic chip or microfluidic device. Such a controller may have internal and/or external pressure sources. The assay system may also be configured for real time data collection.

Accordingly, the invention provides a method of isolating a rare cell or rare cell cluster. The method includes introducing a fluid sample into a microfluidic device as disclosed herein, and causing the rare cell or rare cell cluster of the fluid sample to traverse the plurality of capture zones to the collection well, thereby isolating the rare cell or rare cell cluster.

In embodiments, the cells of the sample may be treated with an agent that degrades cell clusters to provide for cells that are separated and individual single cells. The cells may be treated prior to (e.g., upstream of) or after (e.g., downstream of) separation within the separation channel (50). An agent that degrades cell clusters includes those that degrade proteins that may be associated with the surface of cells that promote cellular aggregation. In one embodiment, the cells may be enzymatically treated to facilitate fibrinolysis. As used herein, fibrinolysis is intended to mean the enzymatic process wherein fibrin and/or products of coagulation, such as fibrin clots and the like are degraded. In one embodiment, degradation by fibrinolysis is performed by treatment of rare cells with the enzyme plasmin. A variety of natural and synthetic plasmins are well known in the art and may be used with the methods of the present invention so long as the enzyme retains some role in fibrinolysis. In another embodiment, fibrinolysis is produced by enzymatic activation of plasminogen.

In addition to enzymatic degradation cells and proteins aggregated to the surface of rare cells and rare cell clusters, may be treated mechanically, electrically, or chemically. For example, mechanical forces may be used to shear cells and proteins aggregated to their surface. Additionally, treatment with a variety of electrical forces may be utilized such as, but not limited to, electromagnetic, electrostatic, electrochemical, electroradiation, ultrasonic forces, and the like. Electromagnetic radiation may include application of radiation from any region of the electromagnetic spectrum.

In one embodiment, mechanical forces sufficient to breaking up agglomerated rare cell clusters may be generated within the device. This may be performed, for example by generating appropriate physical forces on the cell clusters of a fluid sample flowing through the device by microscale features which may be included along the flow path. Accordingly, rare cells and rare cell clusters may be treated enzymatically, chemically, or the like, after isolation by the device, as well as in the microfluidic device itself.

The total number of isolated rare cells is dependent, in part, on the initial sample volume. In various aspects, revealing of rare cells in a wide range of initial sample volumes is sufficient to produce a number of rare cells capable of providing clinically significant results. As such, the initial sample volume may be more or less than about 25 µl, 50 µl, 75 µl, 100 µl, 125 µl, 150 µl, 175 µl, 200 µl, 225 µl, 250 µl, 300 µl, 400 µl, 500 µl, 750 µl, 1 ml, 2 ml, 3 ml, 4 ml, 5 ml, 6 ml, 7 ml, 8 ml, 9 ml or greater than about 10 ml. In an exemplary aspect, the initial sample volume is between about 5 and 10 ml.

Accordingly, in one aspect, the invention provides a composition including a population of rare cells isolated by the microfluidic device as disclosed herein. In one aspect, the composition includes unlysed and/or intact cells. In another aspect, the revealed population includes greater than about 1, 2, 3, 4, 5, 7.5, 10, 50, 100, or 200 rare cells per 100 microliters.

In various embodiments of the present invention, isolated rare cells are analyzed to derive clinically significant data. Analysis of rare cells may be performed by a variety of methods depending of the type of data desired. For example, in various aspects, rare cells may be analyzed by detecting and characterizing the rare cells via assays utilizing recognition and/or binding of cellular components, such as cell surface markers. A variety of assays are contemplated for use with the present invention from which useful data may be derived.

In one embodiment, isolated rare cells may be analyzed via nucleic acid sequence analysis, including whole genome sequencing. Completely sequenced genomes may be produced for an individual patient's rare cells isolated using a device as described herein and normal (non-cancerous) cells obtained from the patient. As discussed further in Example 2, for a number of reasons, it is desirable to conduct single cell whole genome sequencing by combining a procedure similar to "Multiple Annealing and Looping Based Amplification Cycles" (MALBAC) with a next generation sequencing (NGS) technology. For example, a whole genome amplification (WGA) method has been reported that allows unbiased uniform amplification of the entire human genome from a single cell (Zong et al. *Science* Vol. 338, No. 6114, 2012, pp. 1622-1626). The example WGA method is referred to as MALBAC and can be applied to single human cells. Essentially, MALBAC is a method to pre-amplify the entire genome from an individual cell which sufficient uniformity to accurately sequence greater than 85% of the original cell's genomic DNA. Following the MALBAC process, sufficient quantities of DNA are available for use on any suitable next generation DNA sequencing platform, for example, the Ion Torrent System™ (Thermo Fisher Scientific, Inc.).

Accordingly, in yet another aspect, the invention provides a method of obtaining genetic information from a subject. The method includes: a) obtaining a blood sample from the subject; b) isolating a rare cell or rare cell cluster from the blood sample by introducing the sample into a microfluidic device as described herein and causing the rare cell or rare cell cluster of the sample to traverse the plurality of capture zones to the collection well; c) lysing the isolated cells; and d) obtaining genetic information from the cell lysate, thereby obtaining genetic information from the subject. In embodiments, the genetic information is obtained from a single isolated rare cell from the sample. In additional embodiments, the method may further include comparing the genetic information from one single isolate rare cell to genetic information obtained from another single isolated rare cell from the same subject.

Specialized bioinformatics tools may further be utilized for analysis of the sequencing data generated by WGS as discussed further in Example 3. In this manner is it desired to determine and identify clinically relevant genetic driver mutations within a cancer stem cell as opposed to non-disease-related genetic differences. As such, a bioinformatics platform(s) which may be utilized in the invention include those from Cypher Genomics, Inc. as discussed in more detail in Example 3.

In another embodiment, isolated rare cells are analyzed via image analysis. As used herein, image analysis includes any method which allows direct or indirect visualization of rare cells. For example, image analysis may include, but not limited to, microscopic or cytometric detection and visualization of cells bound to a solid substrate, flow cytometry, fluorescent imaging, and the like. In this manner, various parameters of a rare cell may be determined, analyzed and compared to that of a normal cells, including, for example, cellular morphology, such as size and shape.

In various embodiments, a variety of cell surface markers may be used as cell capture reagents to detect and analyze rare cells and rare cell clusters. Cell surface markers may include, but are not limited to surface antigens, transmembrane receptors or co-receptors, macromolecules bound to the surface, such as bound or aggregated proteins or carbohydrates, internal cellular components, and the like. In one embodiment, the cell surface marker is a rare cell specific marker. Various receptors have been found to be expressed or over expressed only in particular types of cancers. In various embodiments of the invention cell surface markers may include one or more of CD44, CD47, MET, EGFR, HER2, ERCC1, CXCR4, ROR1, EpCAM, E-Cadherin, Mucin-1, Cytokeratin, PSA, PSMA, RRM1, Androgen Receptor, Estrogen Receptor, Progesterone Receptor, IGF1, EML4, or Leukocyte Associated Receptor (LAR). Further, cell surface markers may be utilized that are specific to particular cell types. For example, useful endothelial cell surface markers include CD105, CD106, CD144, and CD146, while useful tumor endothelial cell surface markers include TEM1, TEM5, and TEM8.

As discussed herein, analysis of isolated cells to generate clinically significant information may include a variety of methodologies. These include, but are not limited to image analysis, cell number analysis, cell morphology analysis, polymerase chain reaction (PCR) analysis, sequence analysis, DNA analysis, RNA analysis, gene expression profiling, proteome analysis, metabolome analysis, immunoassays, and nuclear exclusion analysis.

Detection and analysis of rare cells, using the methods of the invention, is useful in assessing cancer prognosis and in monitoring therapeutic efficacy for early detection of treatment failure that may lead to disease relapse. In addition, cellular analysis according to the invention enables the detection of early relapse in presymptomatic patients who have completed a course of therapy. This is possible because the presence of rare cells has been associated and/or correlated with tumor progression and spread, poor response to therapy, relapse of disease, and/or decreased survival over a period of time. Thus, enumeration and characterization of rare cells provides methods to stratify patients for baseline characteristics that predict initial risk and subsequent risk based upon response to therapy.

Accordingly, in another embodiment, the invention provides a method for diagnosing or prognosing cancer in a subject. The method includes isolating rare cells of the subject as described herein. The cells may then be analyzed to diagnose or prognose cancer in the subject. As such, the methods of the present invention may be used, for example, to evaluate cancer patients and those at risk for cancer. In any of the methods of diagnosis or prognosis described herein, either the presence or the absence of one or more indicators of cancer, such as, a cancer cell, or of any other disorder, may be used to generate a diagnosis or prognosis.

The term "cancer" as used herein, includes a variety of cancer types which are well known in the art, including but not limited to, dysplasias, hyperplasias, solid tumors and hematopoietic cancers. Many types of cancers are known to metastasize and shed circulating tumor cells or be metastatic, for example, a secondary cancer resulting from a primary cancer that has metastasized. Additional cancers may include, but are not limited to, the following organs or systems: brain, cardiac, lung, gastrointestinal, genitourinary tract, liver, bone, nervous system, gynecological, hematologic, skin, breast, and adrenal glands. Additional types of cancer cells include gliomas (Schwannoma, glioblastoma, astrocytoma), neuroblastoma, pheochromocytoma, paraganlioma, meningioma, adrenalcortical carcinoma, medulloblastoma, rhabdomyoscarcoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia; and skin cancers including malignant melanoma, basal cell carcinoma, squamous cell carcinoma, Karposi's sarcoma, moles dysplastic nevi, lipoma, angioma, dermatofibroma, keloids, sarcomas such as fibrosarcoma or hemangiosarcoma, and melanoma.

In various aspects, analysis of a subject's rare cell number and characterization may be made over a particular time course in various intervals to assess a subject's progression and pathology. For example, analysis may be performed at regular intervals such as one day, two days, three days, one week, two weeks, one month, two months, three months, six months, or one year, in order to track level and characterization of circulating epithelial cells as a function of time. In the case of existing cancer patients, this provides a useful indication of the progression of the disease and assists medical practitioners in making appropriate therapeutic choices based on the increase, decrease, or lack of change in circulating epithelial cells, such as the presence of rare cells in the patient's bloodstream. Any increase, be it 2-fold, 5-fold, 10-fold or higher, in the rare cells over time decreases the patient's prognosis and is an early indicator that the patient should change therapy. Similarly, any increase, be it 2-fold, 5-fold, 10-fold or higher, indicates that a patient should undergo further testing such as imaging to further assess prognosis and response to therapy. Any decrease, be it 2-fold, 5-fold, 10-fold or higher, in the rare cells over time shows disease stabilization and a patient's response to therapy, and is an indicator to not change therapy. For those at risk of cancer, a sudden increase in the number of circulating epithelial cells detected may provide an early warning that the patient has developed a tumor thus providing an early diagnosis. In one embodiment, the detection of rare cells increases the staging of the cancer. In some embodiments, the cancer is bladder cancer, bone cancer, brain cancer, breast cancer, cervical cancer, colon cancer, esophageal cancer, gastric cancer, glioma, head and neck cancer, kidney cancer, leukemia (e.g., acute myeloid leukemia (AML)), liver cancer, lung cancer, lymphoma, melanoma, mesothelioma, medulloblastoma, ovarian cancer, pancreatic cancer, prostate cancer, rectal cancer, skin cancer, testicular cancer, tracheal cancer, and vulvar cancer.

Additional analysis may provide data sufficient to make determinations of responsiveness of a subject to a particular therapeutic regime, or for determining the effectiveness of a candidate agent in the treatment of cancer. Accordingly, the present invention provides a method of determining responsiveness of a subject to a particular therapeutic regime or determining the effectiveness of a candidate agent in the treatment of cancer by isolating rare cells of the subject as described herein and analyzing cells. For example, once a drug treatment is administered to a patient, it is possible to determine the efficacy of the drug treatment using the methods of the invention. For example, a sample taken from the patient before the drug treatment, as well as one or more cellular samples taken from the patient concurrently with or subsequent to the drug treatment, may be processed using the methods of the invention. By comparing the results of the analysis of each processed sample, one may determine the efficacy of the drug treatment or the responsiveness of the patient to the agent. In this manner, early identification may be made of failed compounds or early validation may be made of promising compounds.

In various embodiments, channels of the present invention may be generated by a number of methods known in the art. For example, channels may be generated via photolithography, etching, 3D-printing and the like.

The following examples are provided to further illustrate the embodiments of the present invention, but are not intended to limit the scope of the invention. While they are typical of those that might be used, other procedures, methodologies, or techniques known to those skilled in the art may alternatively be used.

Example 1

Rare Cell Capture and Isolation Using Microfluidic Chip Device

Recent scientific publications suggest that CSCs are responsible for distant tumor metastasis with several different cancer types, and can ultimately result in the death of the patient. CSCs can be found within several areas of the patient, including the primary tumor, proximal lymph nodes adjacent to the tumor, and circulating in the blood stream. Capture and isolation of the CSCs whether in tumor, lymph node, or whole blood is difficult using conventional techniques since the number of CSCs may only range from 1-20 cells among billions of other cancerous and non-cancerous cells.

Capture and Isolation Solution

Recent studies have identified a very specialized circulating tumor cell (CTC), also referred to as a metastasis-initiating cell (MIC) with 3 specific surface proteins, that was shown to correlate with a higher number of metastatic sites in humanized mouse xenografts when compared with other CTCs (Bacelli et al., *Nature Biotech.*, Vol. 31, No. 6, June 2013). The publication suggests that nucleated cells with surface proteins of CD44, CD47, and MET, when isolated and infused into mouse xenographs, produced the highest number of distant metastatic sites in bone, lung, and liver. The data presented provides the strongest evidence to date that the authors have identified CSCs and the role of these highly specialized cells play in the spread of cancer.

The Baccelli publication utilized a flow cytometry method to select and isolate these specialized cells. However, flow cytometry methods have several significant limitations that make the routine capture and study of these specialized cells extremely difficult. These limitations include: a) single capillary flow path allowing individual cells to pass the detector is too slow for large sample volumes, e.g., 10 mls of whole blood; b) sample preparation requires clusters of cells to be disassociated or broken down into individual cells for optimal flow cytometry performance; and c) sample preparation steps, prior to analysis are laborious and technique dependent.

Given the inherent limitations of traditional flow cytometry, a new microfluidic device of the present invention, in one embodiment referred to herein as "CSC$^{3TM}$", addresses the limitations of flow cytometry while providing highly purified, individual cancer stem cells and/or cancer stem cell clusters. The CSC$^{3TM}$ device utilizes three separate cell capture zones in addition to an electro-osmotic separation zone to isolate both individual cancer stem cells and/or cancer stem cell clusters (i.e., small grouped cell aggregates from which new metastatic tumors likely arise).

Patient samples, for example, 10 mls of whole blood (stored in heparinarized collection vial) can be loaded directly onto the CSC$^{3TM}$ device via a luer lock fitted plastic syringe that also has a luer to capillary adapter. A motorized syringe pump is used to maintain a steady specimen infusion flow rate. Other patient sample types such as cell suspensions from a primary tumor (via surgical dissection or fine needle aspiration), or dissected lymph nodes, as an alternative to whole blood, can be infused into the device at a suitable linear flow rate, e.g., 27.5 µl/min.

A major design feature of the CSC$^{3TM}$ device is the three separate cell capture stages or zones, each with a unique capture reagent (e.g., an antibody or aptamer), bound to an alginate hydrogel, which can retain cells displaying surface antigens specific for the bound antibodies. After cell binding, the alginate hydrogel can then be dissolved to allow the cells to move to a wash area, followed by transport to the remaining downstream cell capture zones to further purify the CSCs from contaminating cell types. The final isolation and transport of CSCs into individual wells is performed using, for example, electro-osmotic flow, which is very similar to traditional gel electrophoresis technology. Once the cells of interest are in their respective individual wells, cells may be aspirated into pipette tips and genetic sequencing methods can be initiated on highly purified individual cells or the few cells within a cancer stem cell cluster.

Another design feature of the CSC$^{3TM}$ device is the incorporation of Peltier frozen valves, which are a type of re-useable microfluidics valve that allows liquid flow depending upon whether that specific section of the fluid channel is frozen or thawed. In the device illustrated in FIG. 1, a peltier thermo-electric cooling valve is incorporated into five localized areas, and each valve can be controlled to allow buffers and cells to be readily transported through the microfluidic channels of the device.

Figure 2:
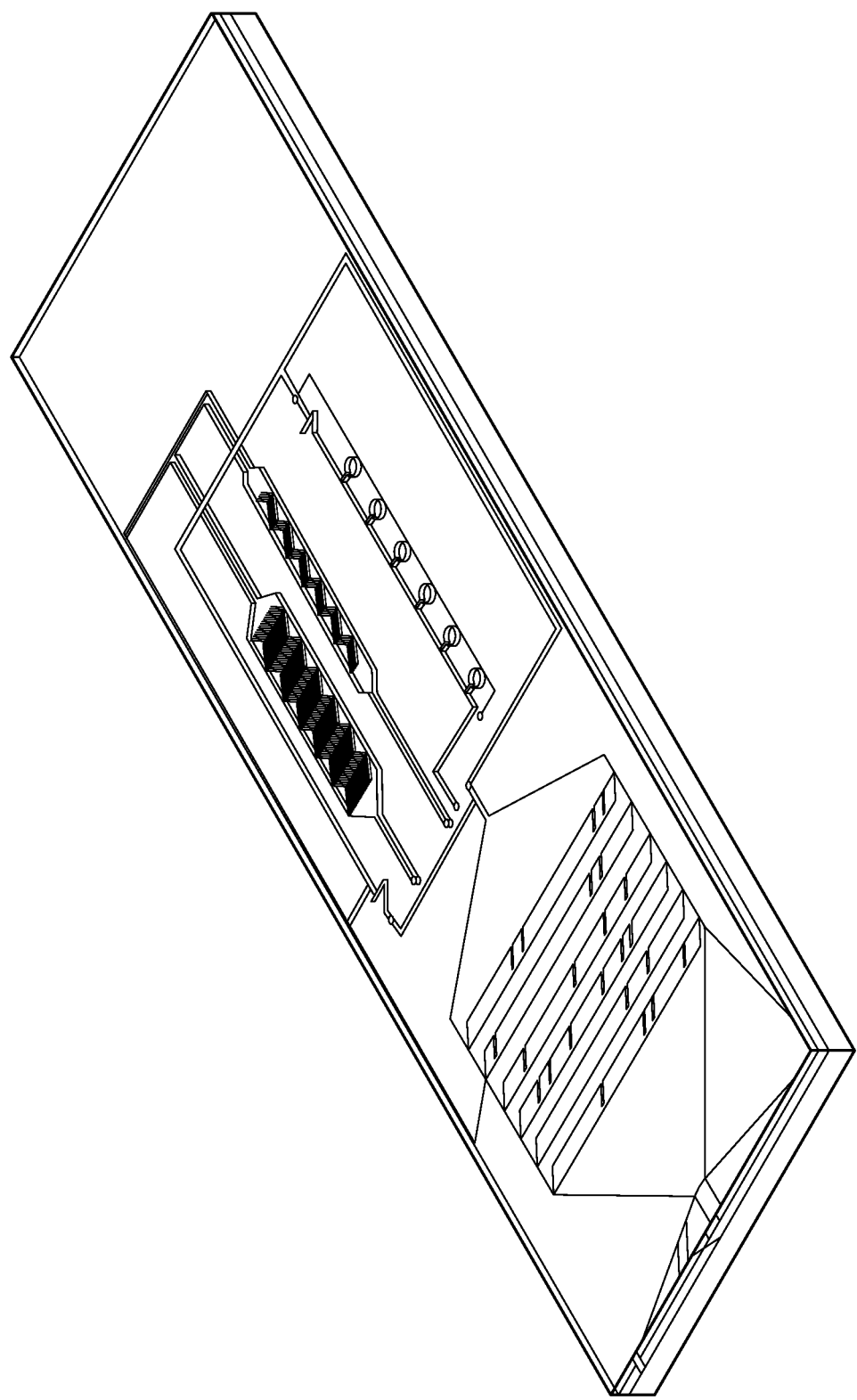
FIG. 2 is an illustration of a microfluidic capture device in one embodiment of the invention that has dimensions of 75 mm×25 mm.
Figure 3:
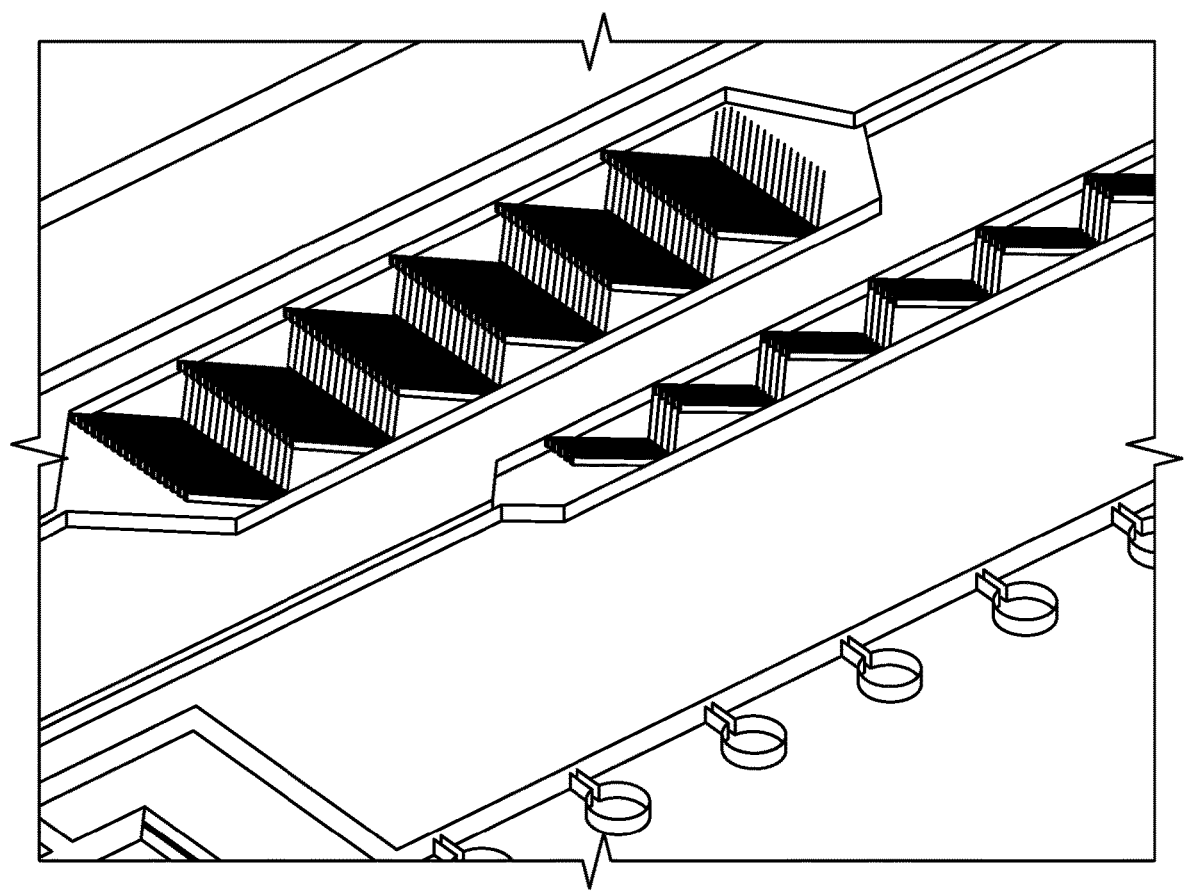
FIG. 3 is an illustration of a representative view of herringbone patterns within the microfluidic flow channels of the capture stages of a microfluidic device in one embodiment of the invention. Each channel may be coated, for example, with an alginate hydrogel that has capturing agents, such as antibodies or other bioaffinity moieties, bonded via covalent or affinity linkage that are specific for the targeted surface protein antigen.
Figure 4:
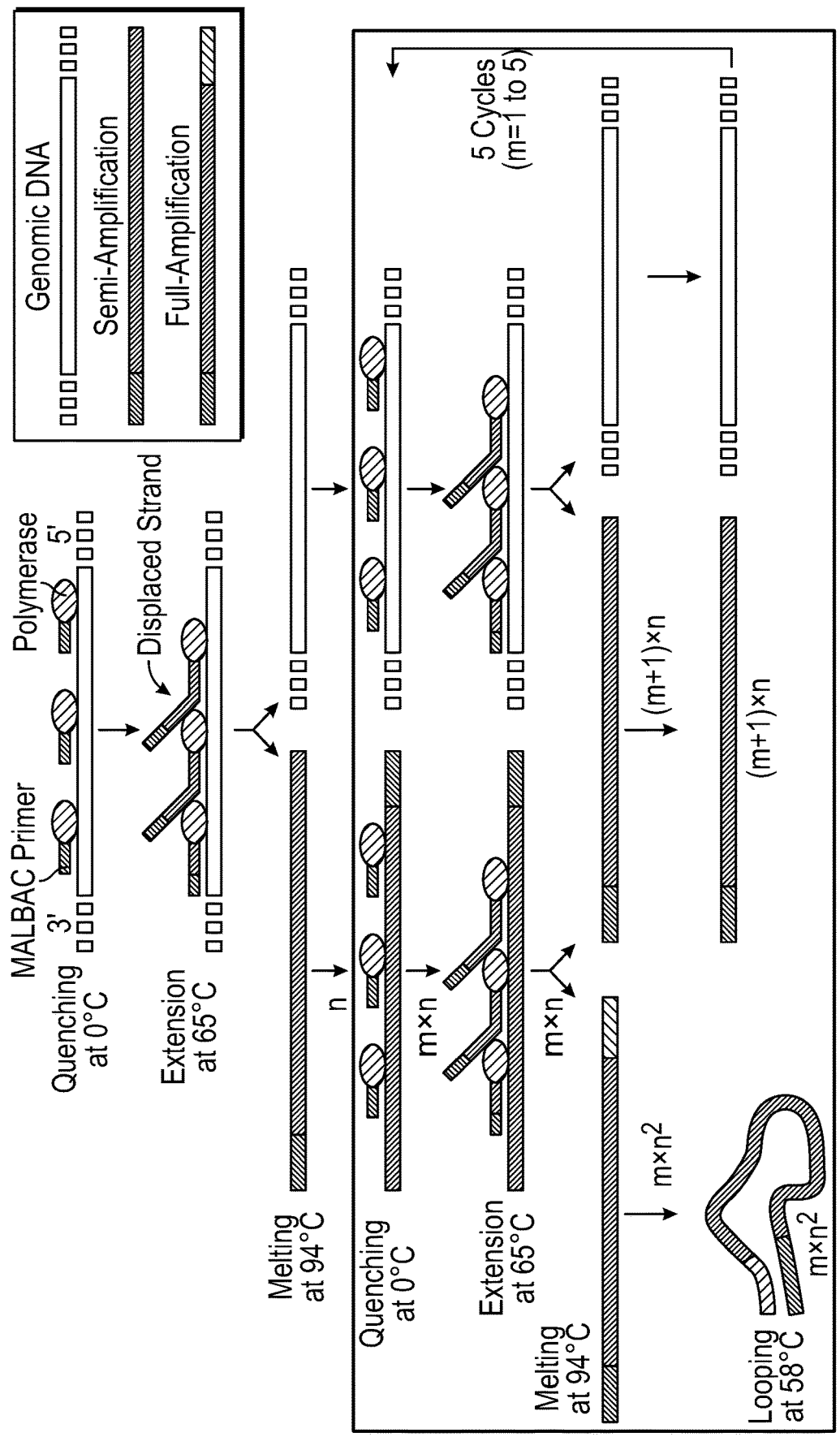
FIG. 4 illustrates an example methodology called Multiple Annealing and Looping Based Amplification Cycles (MALBAC) which can generate from a single rare cell, a genomic DNA library for subsequent genetic analysis as described in Example 2.
Figure 6:
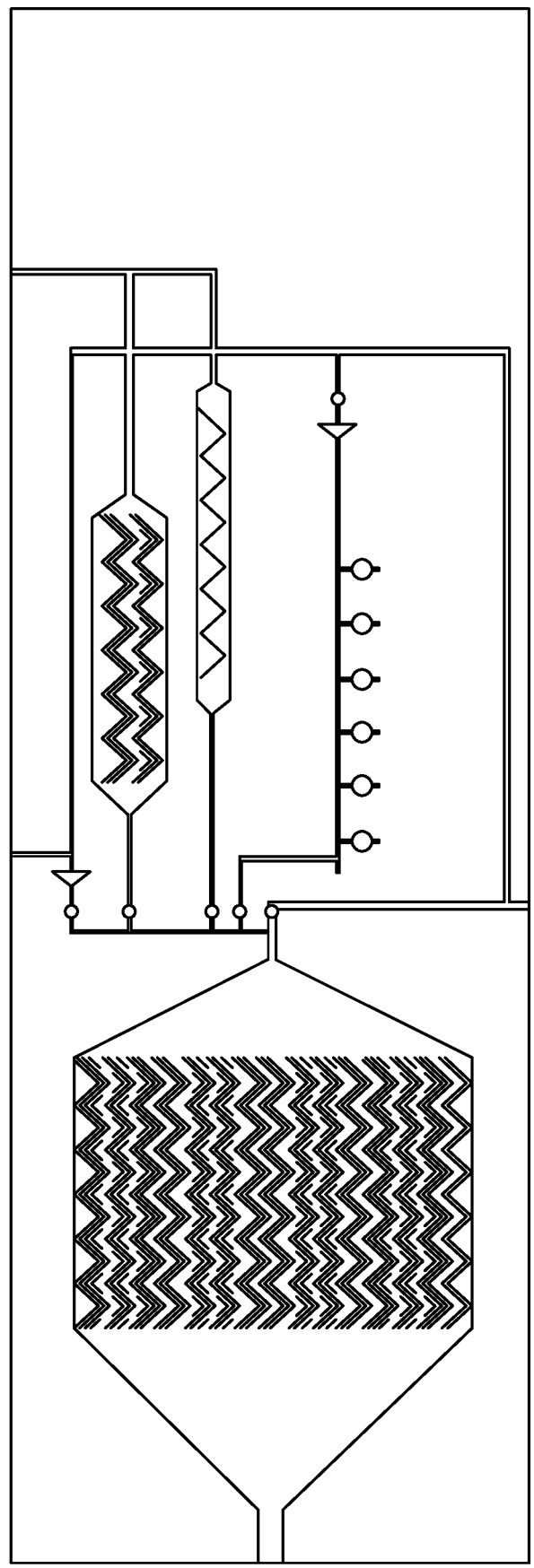
FIG. 6 is a schematic representation of a microfluidic device in one embodiment of the invention.
Figure 7:
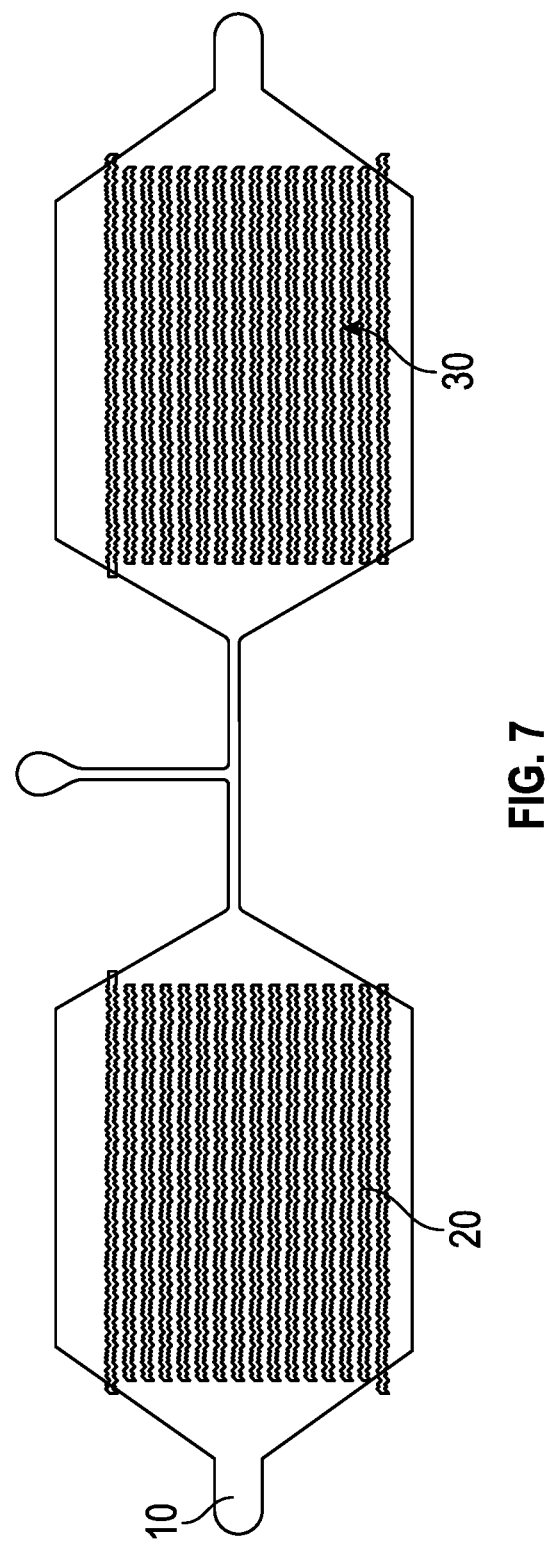
FIG. 7 is a schematic representation of a microfluidic device in one embodiment of the invention. The channels are produced by 3D printing. All channel depths range=500-1000 µm; Channel wall width range=20-350 µm; Open FIB channel width range=200-475 µm; Flow channel width range=150-500 µm; Port diameter range=1000-2000 µm.
Figure 8:
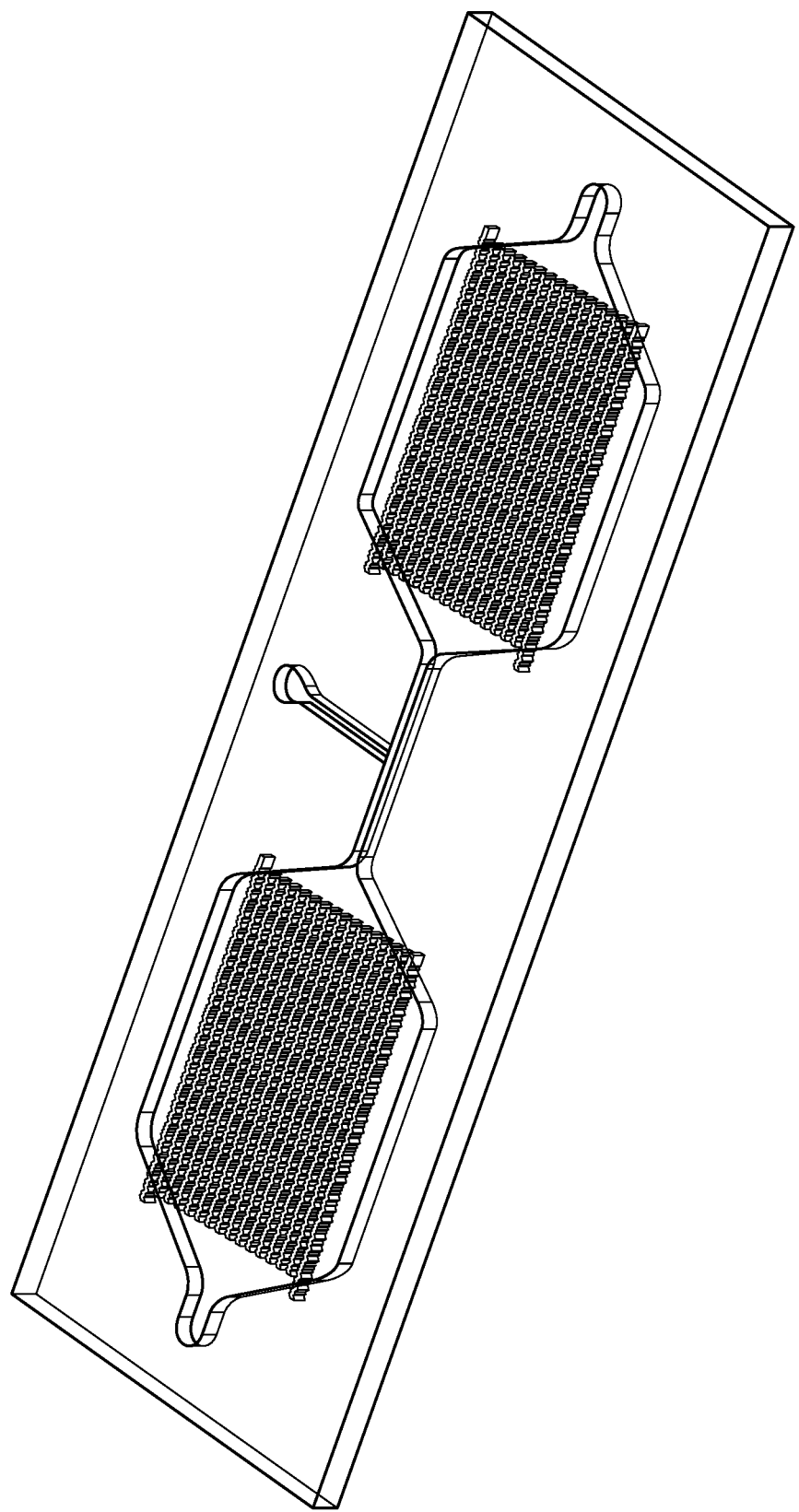
FIG. 8 is a schematic representation of a portion of the microfluidic device of FIG. 7.
Figure 9:
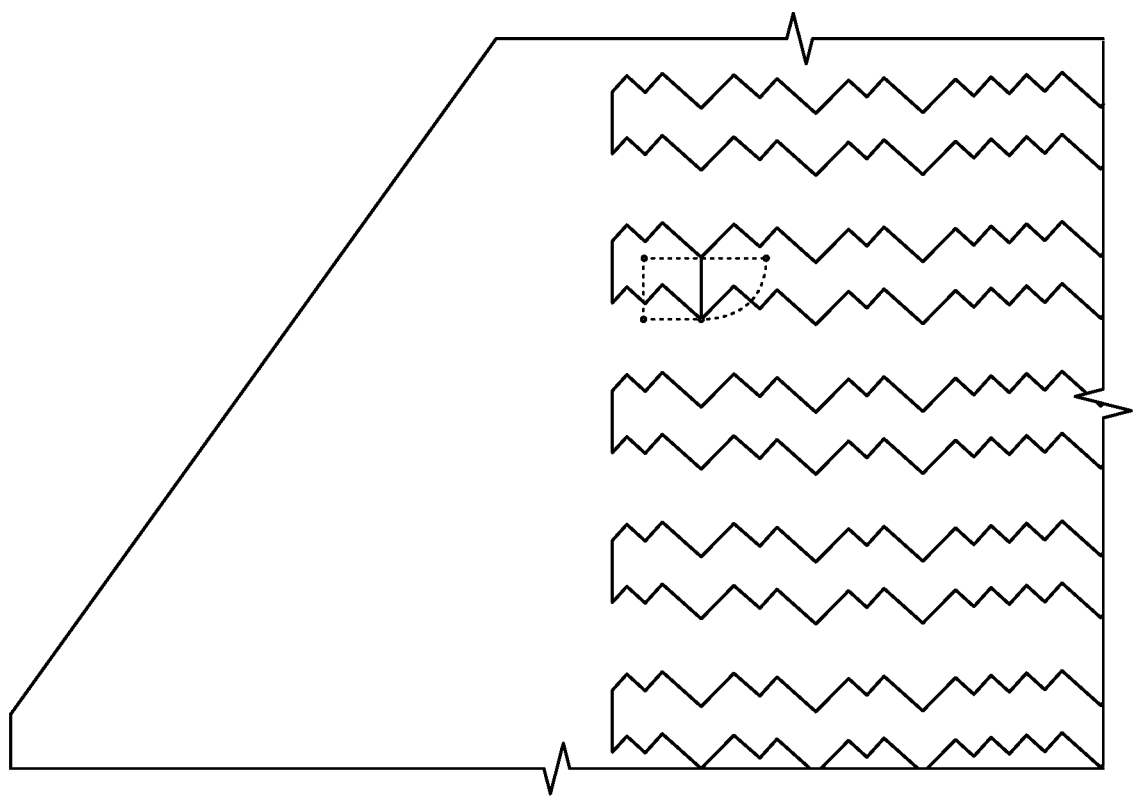
FIG. 9 is a schematic representation of a portion of the microfluidic device of FIG. 7.
Figure 10:
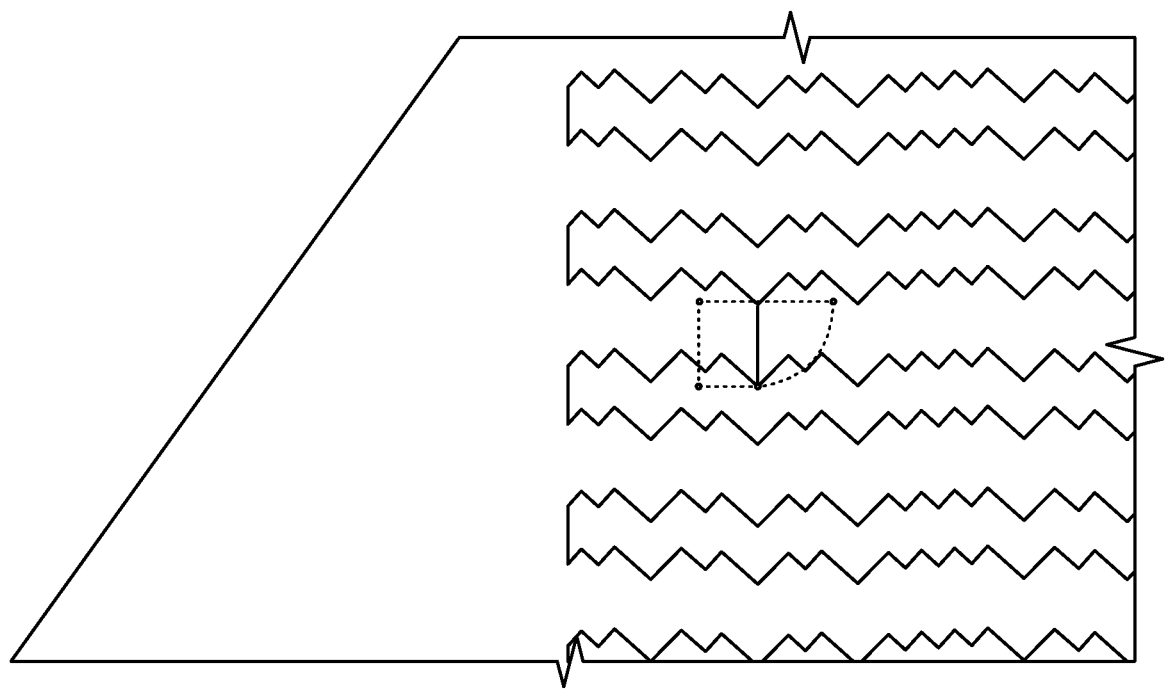
FIG. 10 is a schematic representation of a portion of the microfluidic device of FIG. 7.
Figure 11:
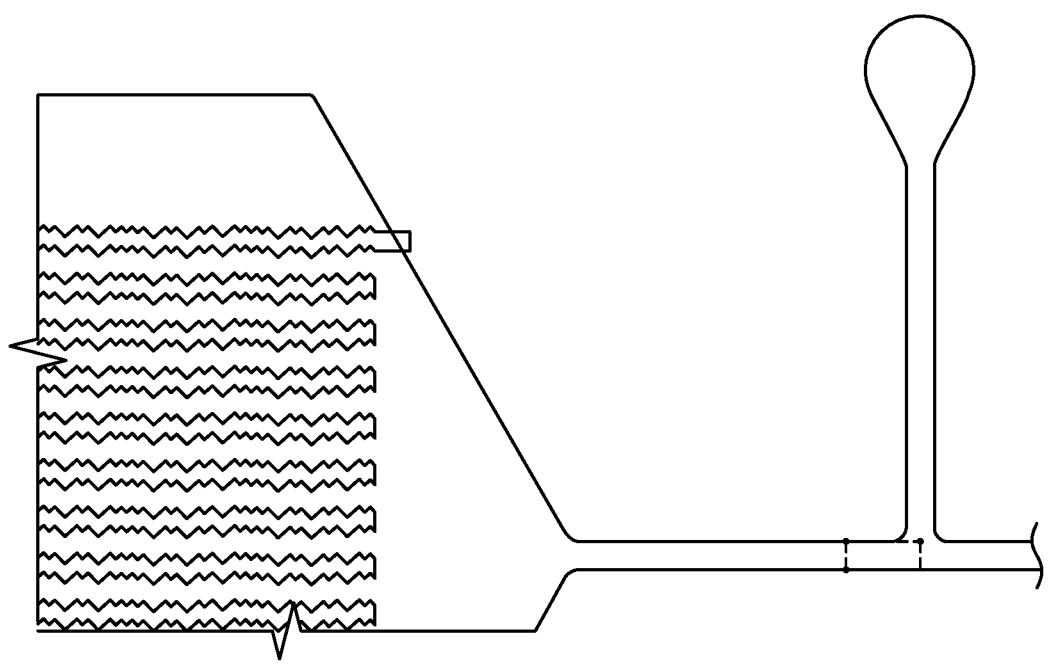
FIG. 11 is a schematic representation of a portion of the microfluidic device of FIG. 7.
Figure 12:
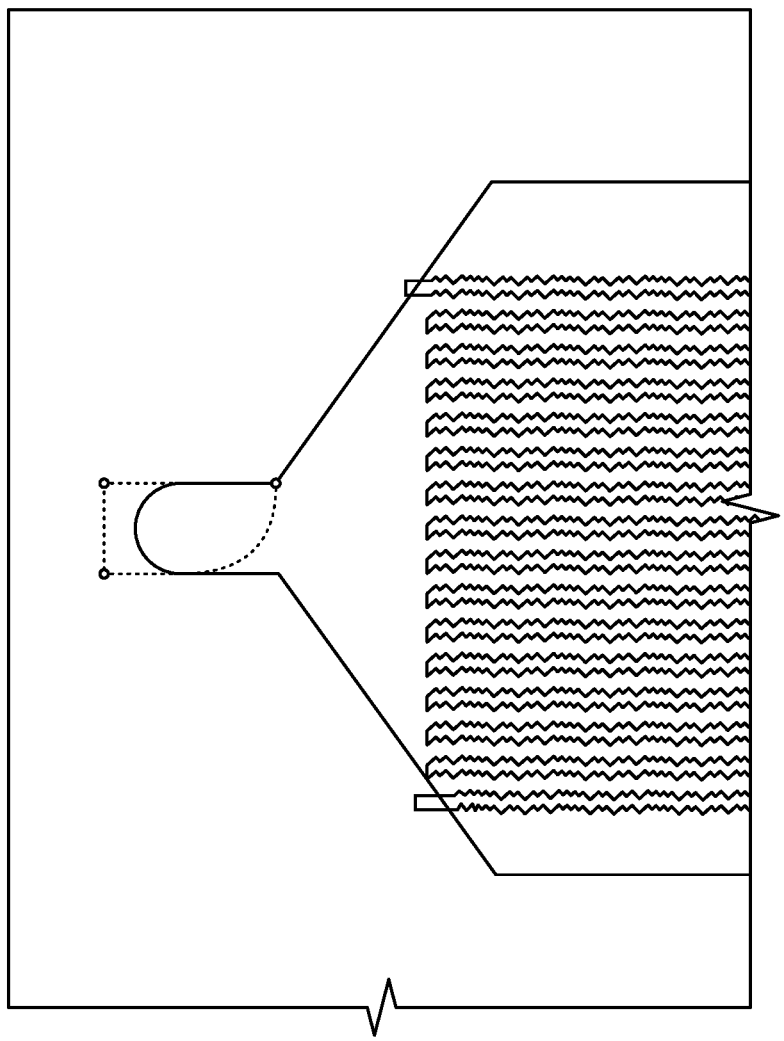
FIG. 12 is a schematic representation of a portion of the microfluidic device of FIG. 7.

The technical drawing for the CSC$^{3TM}$ device is shown in FIG. 2.

Design Advantages

1. The CSC$^{3TM}$ is a highly efficient and cost effective personalized medicine system for the diagnosis and treatment of cancer. The specific design objective is to make a novel microfluidic device capable of capturing both bulk tumor cells and viable cancer stem cell (CSCs) clusters from human whole blood. The ability to capture both living bulk tumor cells and CSCs simultaneously from a single patient specimen is a significant new innovation.
2. Capturing CSC clusters for analysis will provide targeting the few rare cells responsible for cancer metastases. Isolating intact CSC clusters will help in their characterization plus enable direct transfer into in-vivo tumor (human xenograft) animal models for confirmation of the CSCs' metastatic status.
3. Covalently linking or affinity coupling of antibodies (Abs) (or other CSC-specific binding reagents) to the alginate hydrogel is straightforward, allowing binding reagents specific for different CSC antigens to be utilized in the device. This allows the device to be easily configured for different CSCs, depending upon which surface antigens they uniquely present.
4. The capture of viable cells will expedite metastatic confirmation, then the next-generation genetic sequencing (NGS) performed on these CSCs and bulk tumor cells will identify the key DNA driver mutations thus allowing selection of an optimal personalized therapy targeting both cell types.
5. Incorporating an ultra-pure alginate hydrogel coating within the microfluidic channels provides an easily modified, biocompatible surface which demonstrates little non-specific binding.
6. The alginate hydrogel utilized in the device is also a pharmaceutical grade product and thus can be transferred directly into animal model systems, expediting the characterization of the captured cells.
7. The microfluidic devices of the invention incorporate a multi-stage capture process combined with electrophoretic individual cell separation, to capture rare cells. The devices of the invention use at least one, and preferably 2, 3, 4, 5, or more, different sequentially arrayed capture zones each loaded with a different CSC-specific capture reagent to capture individual CSCs, CSC clusters or bulk tumor cells.
8. An advantage of using a multi-stage capture method provides the ability to negatively select out unwanted cell types as part of the sample processing. For example, leukocytes that express CD-45 are well documented contaminating cells that are co-purified in many conventional CTC capture methods. A fourth capture stage would allow the removal of these contaminating cells, if desired, while still utilizing three capture zones each specific for a different unique CSC surface marker.
9. The microfluidic devices of the invention do not require disruption of cell clusters. Flow cytometry-based methods use trypsin or other chaotropic agents to disrupt any cell to cell adhesion since individual cells are required for optimal detection. Trypsin may also disrupt CTC clusters (aka CSCs) by cleaving intercellular surface protein elements holding the group of cells together, thus reducing the ability to identify CSC clusters.
10. The microfluidic devices of the invention provide users the ability to further stain and/or characterize captured cells on the chip. Stains and/or other probe molecules can be added to the individual captured cells/clusters, allowing for easy visualization, functional assay testing, or the like.

11. The presently preferred CSC³™ device bulk building material is polydimethylsiloxane (PDMS), which has low non-specific protein binding and is transparent.
12. The microfluidic devices of the invention are preferably the size of a standard microscope slide (75 mm×25 mm), which along with the PDMS/alginate hydrogel matrix, allows individual cell visualization using an inverted, phase contrast microscope or fluorescence microscope.
13. Conventional methods employ microfluidic channel dimensions of 1 to 2 cell diameters, e.g., about 50 µm. CTC clusters (size estimates from 50-150 µm) would be excluded from channels having such small internal dimensions, which would prevent their isolation and detection. Also, using channels with small internal dimensions (e.g. 50 µm) while perfusing whole blood may cause the red blood cells (RBCs) to lyse. In contrast, the microfluidic devices of the invention utilize much larger diameter channels (e.g., 60-450 µm) for the initial whole blood specimen infusion, thus reducing the risk of RBC lysis.
14. The microfluidic devices of the invention have the ability to isolate highly purified CSCs, which are genetically homogeneous cells, thus improving genetic analysis, for example, whole genome sequencing (WGS) mutation analysis and identification.
15. Flow cytometry-based methods often reuse a detection sheath after sterilization and/or cleaning. Possible patient sample carryover or contamination is thus a risk. The microfluidic devices of the invention are instead single use, disposable units that eliminate any such risk.
16. Flow cytometry-based methods require cells to line up individually as they pass the detector; thus, such methods cannot accurately handle cell clusters or clumps. Flow cytometry also requires lengthy sample preparation procedures, including reagent addition, to break apart cell clusters. The microfluidic devices of the invention do not require the separation of individual cells from clusters or aggregates; indeed, the devices of the invention allow for cell clusters to remain intact for subsequent analysis.

Device Flow Sequence

The microfluidic device of the invention, including the CSC³™ device, utilize at least one, and preferably two (or more) separate cell capture zones in addition to a cell/cluster separation zone (e.g., an electro-osmotic separation zone), to ultimately isolate both individual cancer stem cells in addition to CTC clusters or small grouped cell aggregates. The clusters or cell aggregates are an important morphological characteristic that differentiates cells likely to form new metastatic tumors from other non-progenitor tumor cells. Several of the design features of the device of the present invention are intended to preserve nucleated cell aggregates that exhibit intercellular adhesion to support the clusters. As will be appreciated, all captured cells or cell clusters retained in the final capture wells preferably express the surface antigens bound by the corresponding antibodies (or other capture reagents) used in the device's multiple capture zones. All other cells, such as non-nucleated RBCs or cells with only one of the capture antigens, are eluted as waste from the device during the process of performing an assay on the device.

The following is an example of a flow sequence for the isolation and capture of breast cancer stem cells from whole blood. Utilizing different flow sequences and buffers on a CSC³™ device as shown in FIG. 1 allows many different variations of the device, capable of processing multiple sample types such as frozen tumor or lymph node biopsy specimens to isolate cancer stem cells.

Prior to the addition of any biological specimen, all fluid channels of a CSC³™ device are flushed with phosphate buffered saline (PBS). Proper function of the Peltier frozen valves requires buffer and/or other reagents to be within close proximity of the microfluidic channel immediately above or below the Peltier valve.

The starting flow sequence begins with freezing, i.e., closing of Peltier valves numbers 2, 3, 4, and 5 as labeled in FIG. 2, while keeping Peltier valve 1 thawed (i.e., open). The system is then ready for perfusion with a whole blood specimen. A 10 mL whole blood specimen is taken from a heparinized vacutainer tube that is directly connected to the device via 18 gauge blood infusion tubing attached to the Sample Input 1. Directly infusing the whole blood sample from the primary blood collection tube minimizes the risk of cancer stem cells non-specifically binding to the walls of any other vessel, separate centrifuge tube, or pump cylinder. A vacuum source on the waste vacuum line draws the whole blood specimen through the herringbone channels of capture zone 1 and then to waste since Peltier valve 2 is closed. Target rare cells/clusters with the surface antigen CD-44 are retained in capture zone 1, which has covalently attached, fluorescently labeled antibodies (Ab) to CD-44 cross-linked to an alginate hydrogel laid down as the capture reagent in capture zone 1. The vast majority of cells in the sample are red blood cells (RBCs), which are flushed through capture zone 1 and into waste with minimal lysis since the channel dimensions are sufficiently wide to keep any flow shear forces to a low level.

Following introduction of the whole blood specimen in the CSC³™ device, wash buffer is pulled through the system, again via vacuum (after attaching the wash buffer reservoir to the sample inlet) on the waste line to flush any cellular debris or non-bound cells within capture zone 1 into waste. At this point only cells expressing the CD-44 surface antigen are retained in the device (in capture zone 1).

The next flow sequence begins with freezing of Peltier valves 1, 2, 3, and 4 and thawing or opening Peltier valve 5. An EDTA buffer is then allowed to flow through capture stage 1, which dissolves the calcium cross-linked alginate hydrogel, thus releasing the cells along with the CD-44 bound antibodies still attached to the cells' surfaces. The cells with attached antibodies flow along the path of least resistance, which is the microfluidic channel directly in line with the cell retention element, here, C-Comb filter whose fingers or mesh are spaced so as to retain cells on the upstream side of the device. In this representative embodiment, the C-Comb filter (i.e., cell/cluster retention element) has multiple channels with dimensions of only 5 µm×5 µm; therefore, rare cells and clusters are retained on the upstream side of the filter while unbound antibodies, buffer, cellular debris, etc. will easily pass through. An isotonic wash buffer with calcium chloride is flushed through the system, including through the C-Comb filter to remove residual EDTA-containing buffer and to replenish calcium ions within any retained cell aggregates that may have been involved in intercellular adhesion.

The next flow sequence begins with freezing of Peltier valves 1, 2, and 3 and thawing or opening Peltier valves 4 and 5. Wash buffer is allowed to flow from Input 2, which will flush cells retained by the C-Comb filter into capture zone 2, which contains fluorescently labeled antibodies specific for surface antigen CD-47 that have been covalently bound to an alginate hydrogel present in the capture zone. Cells and cell clusters that lack the surface antigen CD-47 are not retained and allowed to flow to waste. At this point in the flow sequence, only cells with both CD-44 and CD-47 surface antigens are retained by Capture Stage 2. Next, EDTA buffer is pumped through via Input 3 to dissolve the capture zone 2 hydrogel and allow the CD-44+/CD-47+ cells to be retained by the C-Comb filter. Wash buffer with calcium chloride is then flushed through the device via Input 3 to wash away any residual EDTA-containing buffer.

The next flow sequence begins by closing Peltier valves 1, 2, and 4 and opening Peltier valves 3 and 5. The CD-44+/CD-47+ cells retained by the C-Comb filter are then washed with buffer from Input 2 into capture zone 3, which contains fluorescently labeled antibodies for the surface antigen MET covalently attached to the alginate hydrogel present in capture zone 3. Following cell attachment, wash buffer is then pumped through capture stage 3 to wash away MET-cells. EDTA buffer is then pumped through via Input 3 to dissolve the capture zone 3 hydrogel and allow the CD-44+/CD-47+/MET+ cells to be retained by the C-Comb filter. An optional step at this point may be used to wash away any residual EDTA-containing buffer using a calcium chloride wash buffer.

The next flow sequence begins with closing valves 1, 3, and 4 and opening valves 2 and 5. The CD-44+/CD-47+/MET+ cells retained by the C-Comb filter are then washed with buffer through the electrophoretic separation channel and retained by the second C-Comb filter. Once all the retained cells are in the second C-Comb filter, voltage is applied, which causes the cells to migrate independently depending on the size and overall charge on the cell-antibody complexes. If desired, cells can be detected as they pass specific detection points along the separation channel by, for example, conductivity or fluorescence emission from labeled antibodies. As cells of interest pass a collection well, the voltage can be switched, for example, to "+" polarity pole for that collection well, thus changing the electroosmotic flow direction into collection well.

Example 2

Whole Genome Sequencing (WGS) of Individual or Small Numbers of CSCs

Completely sequenced genomes are produced for an individual patient's CSCs and bulk tumor cells isolated using a device according to claim 1 plus normal (non-cancerous) cells obtained from the patient. Because the number of collected CSCs is likely to be low, ranging from 1 to 20 cells per patient sample, since current genomic DNA library preparation kits typically require a minimum of 10 ng of DNA for WGS analysis, a single human diploid cell contains only about 6 pg of genomic DNA (if 10 CSCs are captured, only about 60 pg of initial genomic DNA would be available for sequencing, which is below the current minimum levels of DNA required for library preparation), and since captured CSCs may or may not exhibit a high level of genetic homogeneity, it is desirable to conduct single cell whole genome sequencing by combining a procedure similar to "Multiple Annealing and Looping Based Amplification Cycles" (MALBAC) with a next generation sequencing (NGS) technology. For example, a whole genome amplification (WGA) method has been reported that allows unbiased uniform amplification of the entire human genome from a single cell (Zong et al. *Science* Vol. 338, No. 6114, 2012, pp. 1622-1626). The example WGA method is referred to as MALBAC and can be applied to single human cells. Essentially, MALBAC is a method to pre-amplify the entire genome from an individual cell which sufficient uniformity to accurately sequence greater than 85% of the original cell's genomic DNA. Following the MALBAC process, sufficient quantities of DNA are available for use on any suitable next generation DNA sequencing platform, for example, the Ion Torrent System™ (Thermo Fisher Scientific, Inc.)

Example 3

Bioinformatics Analysis of the CSC/Normal Cell Pairs

The use of specialized bioinformatics is critical for the analysis of the sequencing data generated by WGS, particularly to identify the clinically relevant genetic driver mutations within a cancer stem cell as opposed to non-disease-related genetic differences. One such suite of bioinformatics software is available from Cypher Genomics, (recently acquired by Human Longevity, Inc.) and is intended for use on human whole genome sequences. This sequencing data analysis package performs the following functions.

1. Variant-Impact Prediction—Numerous curated databases are queried to bring to you all pertinent prior knowledge with ease. Up-to-date medical knowledge regarding prior variant associations, including information regarding variants definitively known to be the cause of disease, or variants associated with increased risk facilitates genetic diagnoses. Prior observations, and known frequencies, of variants within different ethnic populations guide searches for novel deleterious variants. Molecular associations, such as known impacts on gene expression or non-disease phenotypes such as drug metabolism, help further prioritize potentially significant variants.

2. Gene-Phenotype Prediction—Occasionally a solid diagnosis based on symptoms can be made, yet when typical gene sets are sequenced no causative mutation is found. By utilizing the genes known to be involved in a disease of interest, all variants within a human genome can be ranked to identify the variant most likely to be causative in an individual's genome.

3. Cypher Analytics—These tools allow an immediate ranking of all variants found in a human genome for association with a known disease. The disease pipeline begins with Cypher Annotations and the Healthy Genome Reference Panel to filter out variants unlikely to cause disease. Variant-Impact Predictions further filter variants unlikely to be functional. Finally, using the gene-phenotype predictions (above), all remaining variants are ranked for association with the disease of interest.

4. Healthy Genome Reference Panel—A more precise determination of rare or novel variants is prepared by comparing genomes against a large panel of healthy genomes, which allows accurate extraction of variants rarely or never seen in healthy individuals.

Example 4

Correlation of the Driver Mutations and Currently Available Targeted Therapies

The final data analysis involves identification of the most appropriate targeted therapy option for a patient. The bioinformatics analysis (see Example 3, above) may reveal one or more mutations in one or more disease-associated genes, for example, the EML4-ALK gene and/or an EGFR gene, both of which mutations have been shown to induce uncontrolled cell growth. Based on the identified driver mutations, therapy options may be: XALKORI® (crizotinib), which inhibits activity of the resulting protein produced by the EML4-ALK gene trans-fusion; and/or TARCEVA® (erlotinib), which inhibits intracellular phosphorylation of a tyrosine kinase associated with the epidermal growth factor receptor (EGFR).

Several additional examples of various targeted therapies against breast cancer stem cells and the on-going clinical trials are listed in FIG. 5 (from Zardavas et al. *Nature Reviews Clin. Oncol.* Vol. 10, April 2013, p. 191).

Example 5

3D Printed Chip

FIGS. 7-12 depict a device of the present invention in which the channels have been generated using 3D-printing techniques. CSC Capture Chip Dimensions (units on images are in millimeters 1.000 mm=1000 μm).

In the embodiment shown in FIGS. 7-12, the device includes a sample addition port (10) and a plurality of capture zones (20 and 30). Sample is provided at port (10) and is then enters the first capture zone (20) which is configured to remove non-rare cells such as white blood cells. This may be accomplished using an anti-CD45 antibody bound to the alginate channels. Sample further progresses to the second capture zone (30) which may be configured to bind rare cells of interest. Alternatively, the device may include one or more additional downstream capture zones.

In some embodiments, the alginate in the first capture zone may be covalently attached to the substrate such that the alginate does not dissolve. At the same time, the alginate in the second capture zone may be non-covalently attached such that it does dissolve. In this manner, cells captured in a specific capture zone may be released while those in another zone may not.

Additionally, one or more additional antibodies may be added through an injection port to flood the capture zone with antibodies for detection. In this manner multiple types of rare cells may be detected in a single capture zone.

Detection may also include harvesting of the cells. This may be accomplished using a hollow needle punch to pierce the chip covering and harvest an individual cell or cluster from the alginate via the hollow needle. The harvested cells may then be used to directly inoculate a mouse xenograft.

The present Example encompasses the following concepts.

1. Using a microfluidic device to capture rare cells and rare cell clusters manufactured using 3D printing technology.
2. Using a covalently bound alginate hydrogel that does not dissolve, in order to retain/remove unwanted, interfering cells in whole blood.
3. Combine one or more capture zones with covalently bound alginate with one or more dissolvable alginate hydrogel capture zones which can release specifically bound cells or cell clusters.
4. Using a needle punch device to specifically isolate cells and/or cell clusters within the alginate hydrogel for direct inoculation into a mouse xenograft.

Example 6

Chip Generation

Materials and Methods

Two methods were used to construct the basic scaffold structure representing the microfluidics chip configuration shown in the Figures, 3D Printing and photolithography.

3D Printing of Chip of FIG. 13

3D Printer used: Objet 30 Scholar®
Specifications: on the World Wide Web at stratasys.com/3d-printers/design-series/objet30
3D Printing technology: PolyJet
3D Printing material: Rigid Opaque Blue (VeroBlue, RGD840) Stratasys 9600 West 76th Street Eden Prairie, Minn. 55344
3D Printed Microfluidic Chip Dimensions (FIG. 13)
Overall chip height: 2.0 mm
Overall chip length: 75 mm
Overall chip width: 25 mm
Circular port diameter: 1000 um
Flow channel dimensions: 500 um (H)×500 um (W)
Open Herringbone channel dimensions: 200 um (W)×150 um (H)
Open Herringbone channel lengths: variable between 500 um-750 um
Extended ridge surrounding all open areas: 150 um (H) rounded FIGS. 13A-13B are illustrations of a microfluidic capture device generated by 3D printing in one embodiment of the invention. FIG. 13A is an expanded view showing a main flow channel and the associated herringbone pattern within the chip which was created using an Objet 30 Scholar 3D Printer® from Stratasys. FIG. 13B depicts two separate Capture Zones 1 and 2 along with three main inlet/outlet fluid ports, 1, 2, 3. Fluid flow may be controlled by turning on/off the fluid ports in different combinations. In this manner flow can be controlled through each side independently or in combination or to move a specimen from one capture zone to another.

Photolithography of Microfluidic Chip of FIG. 18

Dimensions:
Overall chip height: 2.0 mm
Overall chip length: 75 mm
Overall chip width: 25 mm
Circular port diameter: 1000 um
Channel width: 200 um
Channel height overall: 150 um
Herringbone extension height: 50 um
Herringbone groove width: 50 um
Total capture zone volume: 12.26 ul FIGS. 18-19 depict a device of the present invention created using photolithography. Shown in FIG. 18 is a High-Low Herringbone Configuration (HLHC) of the channels produced via photolithography. The configuration includes 2 separate pieces oxygen plasma bonded together to produce the pattern and includes up to 64 channels (32 from each piece) aligned or offset in parallel and having a total volume of 24.24 μL. In addition, all surfaces are polydimethylsiloxane (PDMS) which eliminates the need for a bottom substrate.

Channel Dimensions of the Microchips

Figure 14:
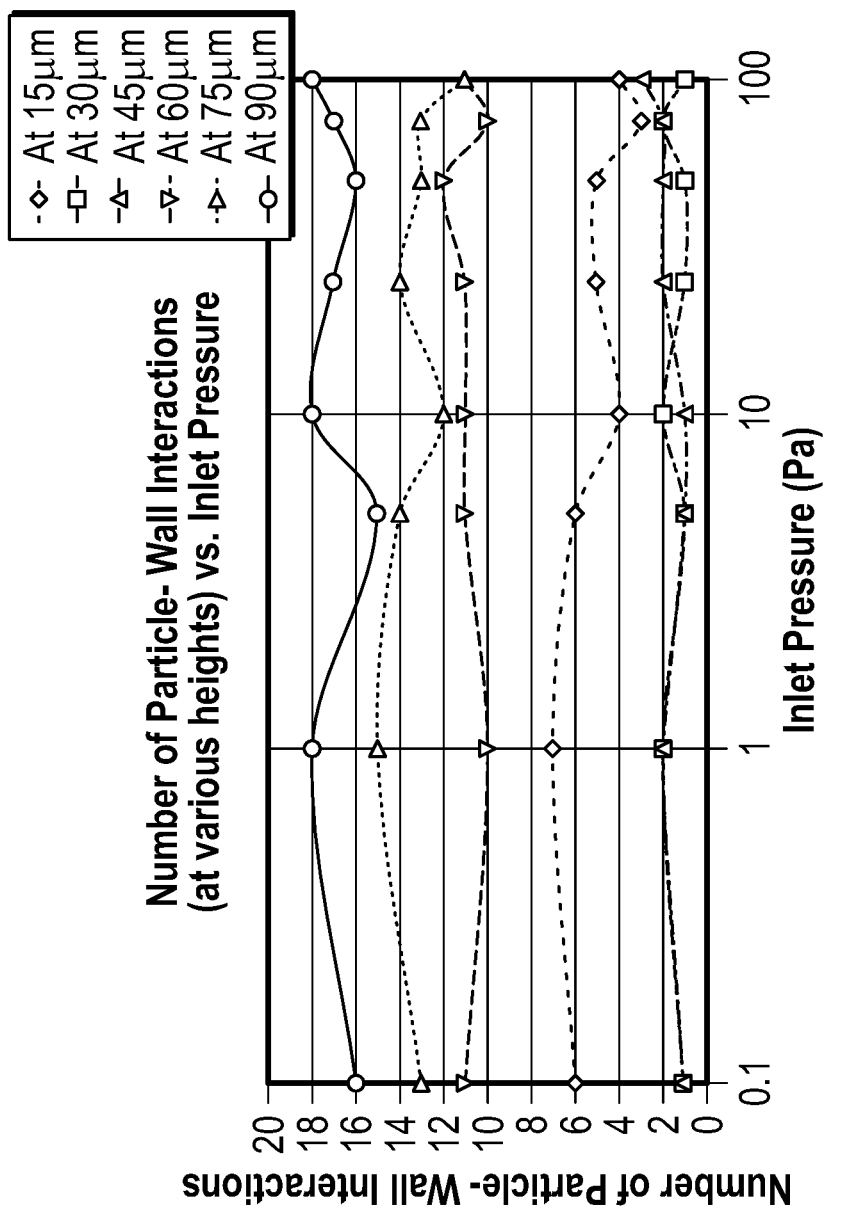
FIG. 14 is a graphic representation showing computer modeling that was performed to optimize channel height dimensions in embodiments of the invention. The modeling was performed assuming different channel height dimensions which incorporated the herringbone ceiling configuration, assuming a particle size of 50 um (i.e., the average rare cell cluster size). The larger channel height simulation consistently shows a greater number of particle-wall interactions.

The individual microfluidic channel dimensions have been optimized to capture rare cell clusters and bulk tumor cell clusters. The average cancer stem cell cluster can range between 3 and 30 cells per cluster. A typical white blood cell diameter is 10-12 um, however a cancer stem cell or rare cell cluster is estimated at 35 um to 60 um in diameter. Current microfluidic capture devices are focused on single cell capture with dimensions that would prevent the capture of rare cell clusters. The microfluidic channels of the present invention are coated with an alginate hydrogel which has been derivatized with a covalently bonded streptavidin bio-affinity molecule. Any antibody with a biotin molecule attached can be easily attached to the alginate-streptavidin modified hydrogel. Since the hydrogel coating within the microfluidic channels is approximately 5um thick, improved binding of rare cells to the immobilized antibody can be achieved by optimizing the number of wall (i.e., hydrogel coating) interactions of the rare cell cluster. Computer modeling (for example FIG. 14) of several parameters were performed which provided a set of dimensions which illustrated that the dimensions described will produce the highest number of particle (i.e., rare cell cluster) wall (i.e., hydrogel coating) interactions.

Example 7

Experimental Methods

Figure 15:
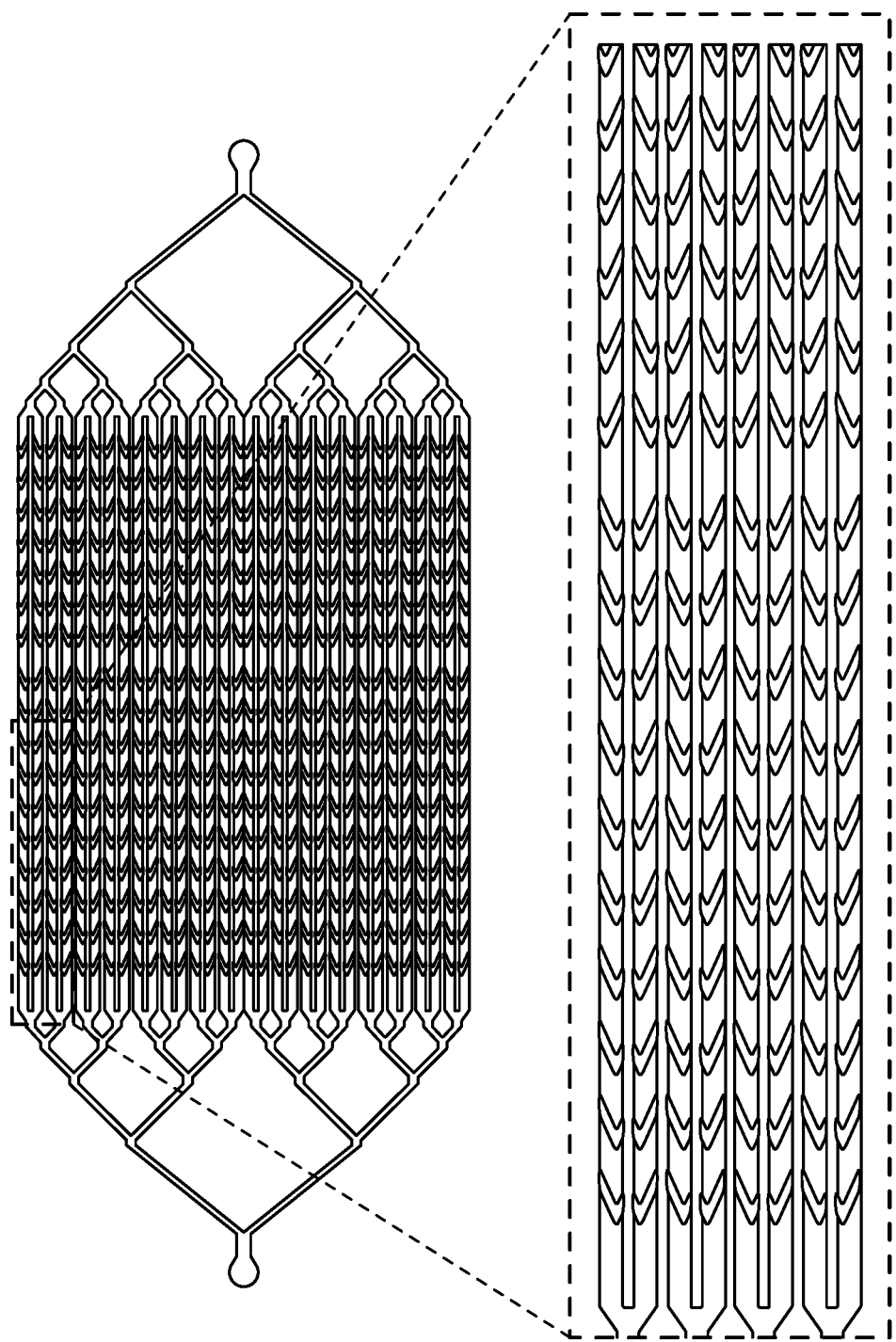
FIG. 15 is a schematic representation of a microfluidic device in one embodiment of the invention generated via photolithography.
Figure 16:
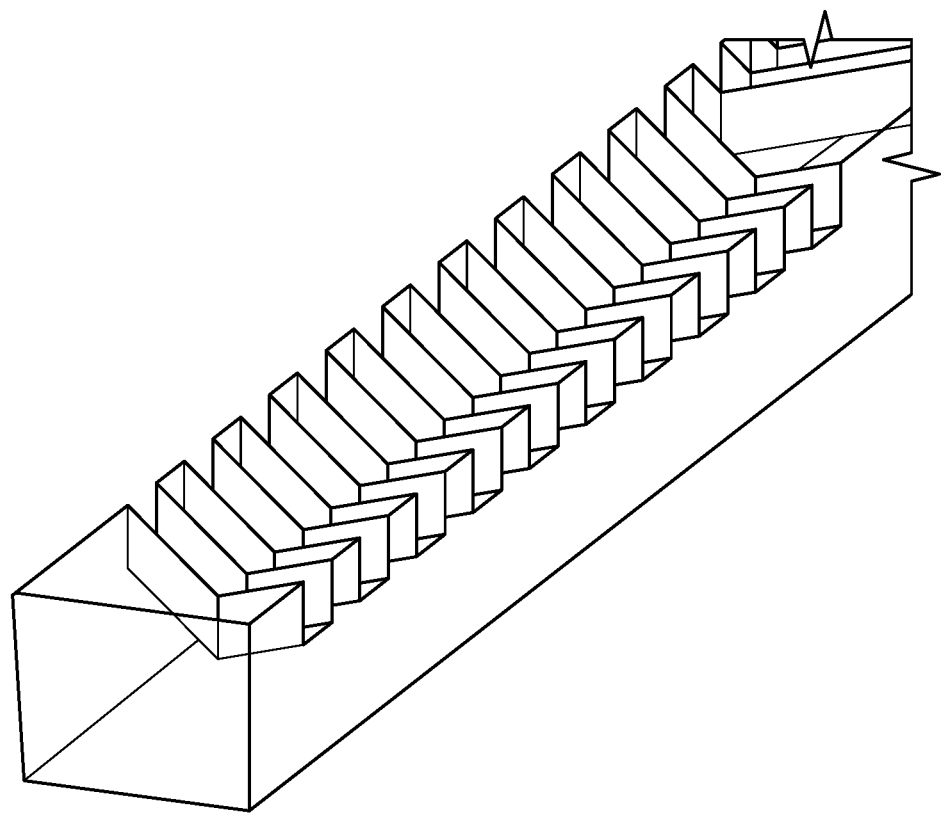
FIG. 16 is a schematic representation of an individual channel of a microfluidic device in one embodiment of the invention.
Figure 17:
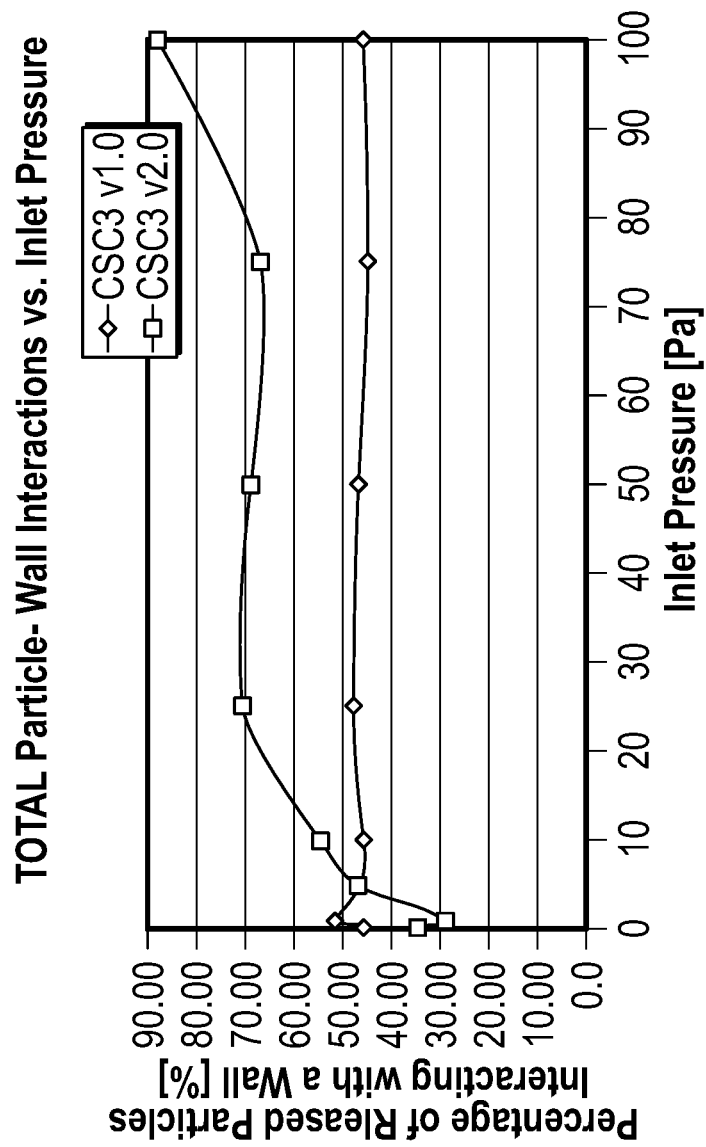
FIG. 17 is a graphic representation showing computer modeling that was performed to optimize particle-wall interactions. Utilizing the herringbone pattern shown in FIG. 16, on the top and bottom of each microfluidic channel produced a dramatic increase in the number of particle (i.e., rare cell cluster) and wall (i.e., hydrogel coating) interactions thereby increasing probability of particle binding and detection.

The following experimental methods may be used with the device of the invention, for example, the device depicted in FIG. 15.

Microfluidic Channel Coating Using a Modified Alginate Hydrogel

The microfluidic channels are coated with an alginate hydrogel which has been derivatized with a covalently bonded streptavidin bio-affinity molecule. Any antibody with a biotin molecule attached can be easily attached to the alginate-streptavidin modified hydrogel. The attached antibody once immobilized on the alginate hydrogel can bind to the surface antigen of a rare cell or rare cell cluster thus retaining the live cell while other cells are washed away. Individual capture zones can be uniquely modified for a specific antibody therefore multiple capture zones used in series can be used to capture multiple surface antigens and therefore multiple cell types.

Alginate Hydrogel Synthesis Procedure

Total volume=50 mls
100 mM MES (2-(N-morpholino)ethanesulfonic acid) buffer pH 7 prepared.
500.2 mg Novamatrix Pronova Ultra-Pure VLVG Alginate™ (G monomer content>60%) (Alg) added to 45 mls of 100 mM MES pH 7.
Vortexed and shaking performed until completely dissolved.
1.45 g of NaCl added to Alg-100 mM IVIES solution.
Mixture left on orbital shaker for 2.5 hrs.
Sequence of addition—dissolve alginate first; then add NaCl; 20.1 mg of 1-Ethyl-3-(3-dimethylaminopropyl)carbodiimid (EDC) added to Alg-MES-NaCl mixture; 54.5 mg of N-hydroxysulfosuccinimide (Sulfo-NHS) was added to Alg-MES-NaCl mixture; gentle shaking and inversion.
5-10 min reaction time was needed for ester to form on Alg-COO-groups.
Add 4.5 mls of 18 Mohm water added to bring the final Alg-MES-Ester mixture to 50 mls.
Target molar ratio of Alg/Streptavidin=100/1; 0.0267 umoles Streptx52800 ug/l umole=1409 ug=1.41 mg Streptavidin.
Mix unlabeled and Cy5 labeled Streptavidin—ZyMAX™ Streptavidin-Cy™ 5 (alternatively, ZyMAX™ Streptavidin-FITC may be used.)
Placed on orbital shaker in a multi-channel reagent trough for 30 minutes=Streptavidin Reaction Time
Dialysis of 50 mls of derivatized Alg-Streptavidin. Prepare 4000 mls of a 10 mM MES pH 7 buffer. Stirred. Dialysis membrane=Spectra/Por Molecular porous membrane tubing (MWCO=6000-8000 kDa; 50 mm wide tubing, ~15 cm length).
Dialysis started in cold room 4 C (after overnight dialysis, the volume inside the dialysis tubing appeared to increase slightly therefore the 1% alginate may be slightly less.)
For Optimal results: Utilize a second dialysis buffer, 4000 mls after 2 hrs of dialysis; recovered ~55 mls of 1% Alg-Strept-Cy5 in 10 mM MES pH 7. Filtered with 0.2 um filter using 10 ml BD syringes, stored at 4 C in foil covered conical centrifuge tubes.

Microfluidic Coating Procedure (of Device of FIG. 15)

Syringe pumps used: Harvard Apparatus Model 11 Plus™
Pre-rinse with 50 mM MES pH 7 @ 990 ul/min for 8 min.
Prepare PDMS surface with 5M CaCl2
Pump 5M CaCl2 @ 990 ul/min for 8 min.
Incubate 1 hr.
50 mM MES pH 7 flush; pump @ 990 ul/min for 8 min; $2^{nd}$ 50 mM MES Syringe loaded; Pump @ 990 ul/min for 8 min.
With chip on Ice Pack; attach 1% Alg-Strept-Cy5 or 1% Alg-Strept-FITC to the channel surface; pump @ 990 ul/min for 4 min; 1 hour incubation.
50 mM IVIES flush; the pump @ 990 ul/min for 8 min.
Cross-link Alg mixture using 100 mM CaCl2; pump @ 990 ul/min for 8 min.
Chip on ice pack for 1 hour incubation.
Remove Ice Pack; 50 mM IVIES flush; then pump @ 990 ul/min for 8 min; rinsed chips with TRIS buffer

Fluorescence Microscopy Images of Microfluidic Coated Chips

Fluorescent Microscope utilized: Zeiss 200M
eGFP (PC3 Prostate Cancer cell line) Ex. 488 Em. 509
 FITC filter set Ex. 495 Em. 518
Hoechst 33342 stain (RPMI-8226 B Cell Multiple Myeloma cell line) Ex. 343 Em. 483
 DAPI filter set Ex. 345 Em. 455
Primary antibody, biotinylated anti-human CD38 (no fluorphore)
Secondary antibody, binds to the primary Ab,
 anti-mouse IgG1-Alexa fluor 594 Ex. 590 Em. 617
 Cy3 filter set Ex. 550 Em. 570

Example 8

Detection of Multiple Myeloma Cells Among an Excess of Prostate Cancer Cells The microfluidic device shown in FIG. 15 was used to detect multiple myeloma cells in a sample having a background population of prostate cancer cells to test specificity of binding. The experimental methods of Example 7 were used with the following cells and antibodies.

Binding of the Primary Antibody to the Alginate Hydrogel

Primary antibody: biotinylated anti-human CD38 biotin
Secondary antibody anti-mouse IgG1 Alexa fluor 594 (secondary antibody binds to the primary antibody)

Cell Lines

RPMI-8226 B Cells (Multiple Myeloma cancer cell line)
PC3 (Prostate cancer cell line with eGFP integrated gene)

Results

The RPMI-8226 B Cells (Hoechst 33342 stains the nuclei of living cells blue) were readily identified within multiple channels. The RPMI-8226 B Cells were captured on the chip using a biotinylated anti-human CD38 antibody bound to the derivatized streptavidin in the alginate hydrogel. The PC3 Prostate Cancer cells have an eGFP expression gene and appeared green using FITC filters. The PC3 cells were also stained with SYTO85 which seen using Cy3 filters. After cells were incubated for 30 min. on the chip, a 20 mM TRIS buffer flush was run for 8 min. @ 200 ul/min., suggesting that non-specifically bound cells would be washed away. Although the RPMI-8226 B cells represent only 10% (100,000 cells) of the 1,000,000 PC3 cells in the injected sample, B cells were preferentially bound compared to the PC3 cells.

Example 9

Detection of Multiple Myeloma

The microfluidic device shown in FIG. 15 was used to detect multiple myeloma cells. The experimental methods of Example 7 were used with the following cells.

Cell Lines

RPMI-8226 B Cells (Multiple Myeloma cancer cell line)

Results

Figure 20:
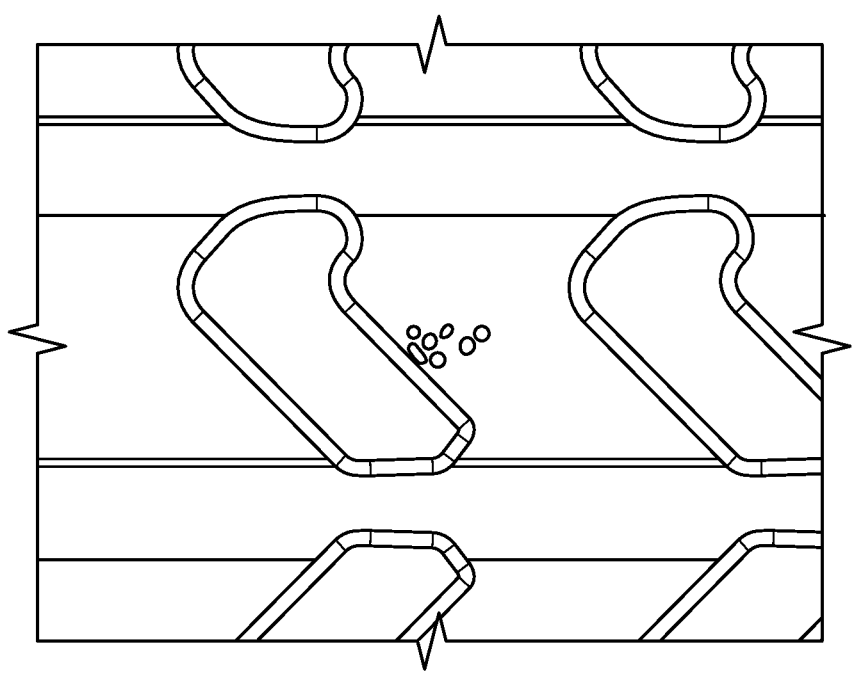
FIG. 20 is an image showing capture of a multiple myeloma cell cluster using the microfluidic device shown in FIG. 15. The image is a magnified view of a captured RPMI-8226 B Cell Multiple Myeloma Cluster. The Hoechst 33342 stained cell nuclei are clearly visible in this image of a RPMI-8226 B Cell cluster captured in the microfluidic channel. Note that individual cells are easily discernable using relatively low magnification. DAPI and Cy3 excitation and emission filter sets were used with a 10× Objective. The microfluidic channel design and dimensions have been selected to capture rare cell clusters while simultaneously capturing single cells.

FIG. 20 is an image showing capture of a multiple myeloma cell cluster using the microfluidic device shown in FIG. 15. The image is a magnified view of a captured RPMI-8226 B Cell Multiple Myeloma Cluster. The Hoechst 33342 stained cell nuclei are clearly visible in this image of a RPMI-8226 B Cell cluster captured in the microfluidic channel. Note that individual cells are easily discernable using relatively low magnification. DAPI and Cy3 excitation and emission filter sets were used with a 10× Objective. The microfluidic channel design and dimensions have been selected to capture rare cell clusters while simultaneously capturing single cells.

Figure 21:
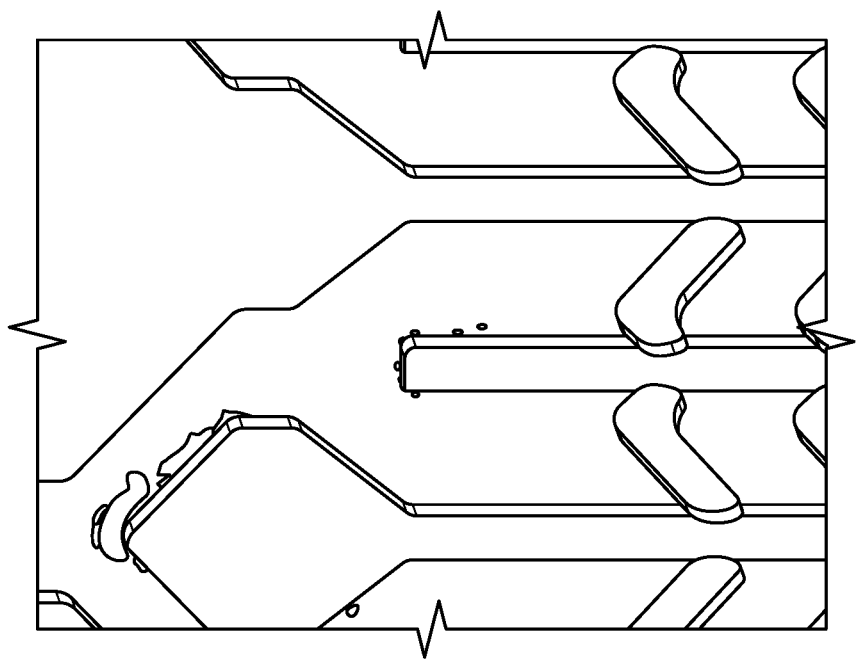
FIG. 21 is an image showing capture of individual multiple myeloma cells using the microfluidic device shown in FIG. 15. The image is a magnified view of several individually captured RPMI-8226 B Cell Multiple Myeloma cells. The Hoechst 33342 stained cell nucleus is clearly visible in this image of the RPMI-8226 B Cells captured in the microfluidic channel (DAPI, FITC, Cy3 Filters, 20× Objective). Individual cells were retained even after washing with 20 mM TRIS buffer pH 7.4 at 200 µl/min for 8 minutes.

FIG. 21 is an image showing capture of a individual multiple myeloma cells using the microfluidic device shown in FIG. 15. The image is a magnified view of several individually captured RPMI-8226 B Cell Multiple Myeloma cells. The Hoechst 33342 stained cell nucleus is clearly visible in this image of the RPMI-8226 B Cells captured in the microfluidic channel (DAPI, FITC, Cy3 Filters, 20× Objective). Individual cells were retained even after washing with 20 mM TRIS buffer pH 7.4 at 200 µl/min for 8 minutes.

Although the invention has been described with reference to the above example, it will be understood that modifications and variations are encompassed within the spirit and scope of the invention. Accordingly, the invention is limited only by the following claims.

What is claimed is:

1. A microfluidic device for capturing a rare cell or rare cell cluster or a bulk tumor cell from a sample having a nonporous substrate that comprises downstream of a sample addition port and arrayed in series:
   a) a plurality of capture zones connected by one or more valved microfluidic channels, wherein each capture zone comprises a releasable cell capture reagent that specifically binds a rare cell surface marker, the cell capture reagent being immobilized on the nonporous substrate, wherein the one or more microfluidic channels connecting a first capture zone and a second capture zone of the plurality of capture zones contains a rare cell or rare cell cluster or bulk tumor cell retention element, wherein the plurality of capture zones contain one or more herringbone geometries, wherein the plurality of capture zones are contained in an aligned high-low herringbone configuration (HLHC), and wherein the HLHC comprises channels that are offset from one another and which fluidly connect with one another in an alternating pattern to produce an increased channel surface area for binding; and
   b) a detector for detecting the rare cell or rare cell cluster or bulk tumor cell bound by the cell capture reagents, wherein the sample is added to the microfluidic device at a flow rate greater than or equal to 27.5 µL/min and the microfluidic device is configured to detect one or more of a rare cell, a rare cell cluster or a bulk tumor cell, simultaneously, and to maintain the rare cell or rare cell cluster or bulk tumor cell alive and viable, and
   wherein the sample is selected from the group consisting of whole blood, blood fractions such as serum and plasma, urine, sweat, lymph, feces, ascites, seminal fluid, sputum, nipple aspirate, post-operative seroma, wound drainage fluid, saliva, synovial fluid, ascites fluid, bone marrow aspirate, cerebrospinal fluid, nasal secretions, amniotic fluid, bronchoalveolar lavage fluid, pleural effusion, peripheral blood mononuclear cells, total white blood cells, lymph node cells, spleen cells, or tonsil cells.

2. The microfluidic device of claim 1, wherein each capture zone comprises a different releasable cell capture reagent that specifically binds a different rare cell surface marker.

3. The microfluidic device of claim 1, wherein the device comprises four or more capture zones, and wherein at least one capture zone comprises a releasable cell capture reagent that specifically binds a non-rare cell surface marker.

4. The microfluidic device of claim 1, wherein the releasable cell capture reagents each comprises an antibody, an antigen-binding antibody fragment or an antigen specific aptamer.

5. The microfluidic device of claim 1, wherein one or more of the releasable cell capture reagents comprise a detectable label.

6. The microfluidic device of claim 1, wherein at least one capture zone includes a dissolvable matrix and at least one capture zone includes a non-dissolvable matrix.

7. The microfluidic device of claim 6, wherein the dissolvable matrix is dissolvable by a chelating agent, enzyme or combination thereof.

8. The microfluidic device of claim 6, wherein the dissolvable matrix is non-covalently bound alginate and the non-dissolvable matrix is covalently bound alginate.

9. The microfluidic device of claim 1, wherein the rare cell surface marker is selected from the group consisting of CD44, CD47, MET, EpCAM, CD34, CD38, CD90, CD19, Stro-1, CD105, CD133, ESA, CD24, ALDH, ALDH1, CD 166, SP, CD20, CD117, A2$\beta$1, EGFR, HER2, ERCC1, CXCR4, E-Cadherin, Mucin-1, Cytokeratin, PSA, PSMA, RRM1, Androgen Receptor, Estrogen Receptor, Progesterone Receptor, IGF1, EML4, Leukocyte Associated Receptor (LAR), and any combination thereof.

10. The microfluidic device of claim 1, wherein the microfluidic device is configured to further capture a bulk tumor cell simultaneously with the rare cell or rare cell cluster.

11. The microfluidic device of claim 10, wherein the rare cell, the rare cell cluster, or bulk tumor cell are harvested by dissolving the non-covalently bound alginate, or are harvested directly from a capture zone using a needle punch.

12. The microfluidic device of claim 1, wherein the microfluidic device is configured to control the fluid flow of the sample to effectuate isolation and harvest of live and viable rare cell, rare cell cluster, or bulk tumor cell.

13. The microfluidic device of claim 1, wherein the microfluidic device is configured to detect one or more of a rare cell, a rare cell cluster or a bulk tumor cell by microscopy or flow cytometry.

14. The microfluidic device of claim 1, wherein the microfluidic device is configured to isolate the rare cell, rare cell cluster, bulk tumor cell, or bulk tumor cell for analysis by one or more of image analysis, cell number analysis, cell morphology analysis, polymerase chain reaction (PCR) analysis, sequence analysis, DNA analysis, RNA analysis, gene expression profiling, proteome analysis, metabolome analysis, immunoassays, nuclear exclusion analysis, whole genome sequencing, or a combination thereof, wherein the isolated rare cell, rare cell cluster, or bulk tumor cell is alive and viable and/or wherein the isolated cell is suitable the analysis which requires living cells.

* * * * *